United States Patent
Hirasawa et al.

(10) Patent No.: US 11,149,074 B2
(45) Date of Patent: Oct. 19, 2021

(54) AZIDE GROUP-CONTAINING FC PROTEIN

(71) Applicant: Ajinomoto Co., Inc., Tokyo (JP)

(72) Inventors: Shigeo Hirasawa, Kawasaki (JP); Masumi Taki, Tokyo (JP)

(73) Assignee: Ajinomoto Co., Inc., Tokyo (JP)

( * ) Notice: Subject to any disclaimer, the term of this patent is extended or adjusted under 35 U.S.C. 154(b) by 218 days.

(21) Appl. No.: 16/177,839

(22) Filed: Nov. 1, 2018

(65) Prior Publication Data
US 2019/0055300 A1 Feb. 21, 2019

Related U.S. Application Data

(63) Continuation of application No. PCT/JP2017/017013, filed on Apr. 28, 2017.

(30) Foreign Application Priority Data

May 2, 2016 (JP) .............................. JP2016-092785

(51) Int. Cl.
| | |
|---|---|
| C07K 14/735 | (2006.01) |
| A61K 39/395 | (2006.01) |
| A61K 47/68 | (2017.01) |
| C12N 15/00 | (2006.01) |
| C07K 19/00 | (2006.01) |
| C07K 16/00 | (2006.01) |
| C07K 5/02 | (2006.01) |
| C12N 15/09 | (2006.01) |
| C07K 16/18 | (2006.01) |

(52) U.S. Cl.
CPC ...... *C07K 14/70535* (2013.01); *A61K 39/395* (2013.01); *A61K 47/6801* (2017.08); *C07K 5/02* (2013.01); *C07K 16/00* (2013.01); *C07K 16/18* (2013.01); *C07K 19/00* (2013.01); *C12N 15/00* (2013.01); *C12N 15/09* (2013.01); *C07K 2317/52* (2013.01); *C07K 2319/30* (2013.01)

(58) Field of Classification Search
CPC .......... C07K 2317/52; C07K 2319/30; A61K 47/68
See application file for complete search history.

(56) References Cited

U.S. PATENT DOCUMENTS

| | | | |
|---|---|---|---|
| 5,428,130 A | 6/1995 | Capon et al. | |
| 7,404,956 B2 | 7/2008 | Peters et al. | |
| 7,737,260 B2 | 6/2010 | Kim et al. | |
| 7,807,619 B2 | 10/2010 | Bertozzi et al. | |
| 8,133,515 B2 | 3/2012 | Boons et al. | |
| 8,431,558 B2 | 4/2013 | Bertozzi et al. | |
| 8,461,298 B2 | 6/2013 | Bertozzi et al. | |
| 8,519,122 B2 | 8/2013 | Jewett et al. | |
| 8,541,625 B2 | 9/2013 | Popik et al. | |
| 8,703,936 B2 | 4/2014 | Jewett et al. | |
| 8,859,629 B2 | 10/2014 | Van Delft et al. | |
| 8,912,322 B2 | 12/2014 | Popik et al. | |
| 8,940,859 B2 | 1/2015 | Boons et al. | |
| 9,085,514 B2 | 7/2015 | Lemke et al. | |
| 2007/0184525 A1 | 8/2007 | Date et al. | |
| 2014/0051836 A1 | 2/2014 | Thanos et al. | |
| 2014/0314711 A1* | 10/2014 | Scheer | C07K 16/2866 424/85.2 |
| 2015/0064745 A1 | 3/2015 | Nonaka et al. | |
| 2017/0008950 A1 | 1/2017 | Capon | |
| 2017/0362341 A1 | 12/2017 | Thanos et al. | |

FOREIGN PATENT DOCUMENTS

| | | |
|---|---|---|
| EP | 1 375 664 A1 | 1/2004 |
| JP | 2008-150464 A | 7/2008 |
| JP | 2009-512641 A | 3/2009 |
| JP | 2009-106267 | 5/2009 |
| JP | 2009-106268 | 5/2009 |
| JP | 2010-122071 | 6/2010 |
| JP | 2015-518905 A | 7/2015 |
| JP | 2015-534996 A | 12/2015 |

(Continued)

OTHER PUBLICATIONS

Janeway CA Jr, Travers P, Walport M, et al. Immunobiology: The Immune System in Health and Disease. 5th ed. New York: Garland Science; 2001. Structural variation in immunoglobulin constant regions. Available from: https://www.ncbi.nlm.nih.gov/books/NBK27106/, (Year: 2001).*

(Continued)

*Primary Examiner* — Peter J Reddig

(74) *Attorney, Agent, or Firm* — Oblon, McClelland, Maier & Neustadt, L.L.P.

(57) ABSTRACT

The present invention provides a means capable of efficiently manufacturing a fused substance of an Fc protein and a substance of interest (for example, a peptide). Specifically, the present invention provides an azide group-containing Fc protein represented by formula (1):

$$N_3\text{-}L_a\text{-}Phe\text{-}L_b\text{-}Fc \qquad (1)$$

wherein $N_3$ represents an azide group;
$L_a$ represents a bond or a divalent group;
Phe represents a residue of phenylalanine or a derivative thereof;
$L_b$ represents a lysine residue or an arginine residue, or a peptide linker containing two or more amino acid residues having a lysine residue or an arginine residue at/on the N-terminus; and
Fc represents an Fc protein;
and the like.

20 Claims, 10 Drawing Sheets
Specification includes a Sequence Listing.

(56) References Cited

FOREIGN PATENT DOCUMENTS

| WO | 02/081694 | 10/2002 |
|---|---|---|
| WO | 2005/103278 A1 | 11/2005 |
| WO | WO 2007/039858 A2 | 4/2007 |
| WO | 2011/024887 A1 | 3/2011 |
| WO | WO 2013/185115 A1 | 12/2013 |
| WO | 2014/004639 | 1/2014 |
| WO | WO 2014/065661 A1 | 5/2014 |
| WO | 2014/126260 A1 | 8/2014 |
| WO | WO 2015/138907 A2 | 9/2015 |

OTHER PUBLICATIONS

International Search Report in Application No. PCT/JP2017/017013 dated Jul. 4, 2017.
Taki Masumi, Leucyl/Phenylalanyl (L/F)-tRNA-Protein Transferase-Mediated Aminoacyl Transfer of a Nonnatural Amino Acide to the N-Terminus of Peptides and Proteins and Subsequent Functionalization by Bioorthogonal Reactions, Peptide Science, Jan. 10, 2007, vol. 88, p. 263-271.
Hirasawa Shigeo, Bioconjugatin Approach Towards Peptide-Fc Fusion Compounds, Peptide Science, Feb. 2016, p. 205-206.
Capon Daniel J. et al., "Flexible antibodies with nonprotein hinges" Proc. Jpn. Acad., Ser. B 87 (2011) pp. 603-616.
Ebisu Keitaro, et al., "N-Terminal Specific Point-Immobilization of Active Proteins by the One-Pot NEXT-A Method", ChemBioChem 2009, 10, pp. 2460-2464.
Junemann Ralf, et al., "In vivo deuteration of transfer RNAs: overexpression and large-scale purification of deuterated specific tRNAs", Nucleic Acids Research, 1996, vol. 24, No. 5 pp. 907-913.
Datta Deepshikha et al., "A Designed Phenylalanyl-tRNA Synthetase Variant Allows Efficient in Vino Incorporation of Aryl Ketone Functionality into Proteins", J. Am. Chem. Soc. 2002, 124, pp. 5652-5653.
Kast, Peter et al., "Amino Acid Substrate Specificity of *Escherichia coli* Phenylalanyl-tRNA Synthetase Altered by Distinct Mutations", J. Mol. Biol. 1991, 222, pp. 99-124.
Kirshenbaum Kent, et al., "Biosynthesis of Proteins Incorporating a Versatile Set of Phenylalanine Analogues", ChemBioChem 2002, No. 02-03, pp. 235-237.
Taki Masumi et al., "Leucyl/Phenylalanyl-tRNA-Protein Transferase-Mediated Chemoenzymatic Coupling of N-Terminal Arg/Lys Units in Post-translationally Processed Proteins with Non-natural Amino Acids", ChemBioChem 2006, 7, pp. 1676-1679.
Roher Alex E., et al., "Morphology and Toxicity of A β-(1-42) Dimer Derived from Neuritic and Vascular Amyloid Deposits of Alzheimer's Disease", The Journal of Biological Chemistry, vol. 271, No. 34, pp. 20631-20635 (1996).
Taki Masumi et al, "Chemoenzymatic Transfer of Fluorescent Non-natural Amino Acids to the N Terminus of a Protein/Peptide", ChemBioChem, 2008, 9, pp. 719-722.
Taki Masumi et al., "Unexpectedly fast transfer of positron-emittable artificial substrate into N-terminus of peptide/protein mediated by wide-type L/F-tRNA-protein transferase" Amino Acids (2015) 47: pp. 1279-1282.
Taki, Masumi, "Synthesis of a cyclic peptide/protein using the NEXT-A reaction followed by cyclization", Chem. Commun., 2011, 47, pp. 9116-9118.
Arimitsu Kenji, et al., "$^{18}$F-Containing Positron Emission Tomography Probe Conjugation Methodoogy for Biologics as Specific Binders for Tumors", Current topics in Medicinal Chemistry, 2016, pp. 2703-2724.
Kawaguchi Jun et al., "Kinetic analysis of the leucyl/phenylalanyl-tRNA-protein transferase with acceptor peptides possessing different N-terminal penitimate residues", FEBS Open Bio 3 (2013), pp. 252-255.
Masumi Taki, "Use of L/F-Transferase to Introduce a Functional Non-natural Amino Acid at the N-Terminus of a Protein", The Chemical Society of Japan, Nov. 30, 2008 (Nov. 30, 2008), vol. 23, No. 3, pp. 3 to 6.
Agard Nicholas J. et al., "A Strain-Promoted [3+2] Azide-Alkyne Cycloaddition for Covalent Modification of Biomolecules in Living Systems", J. Am. Chem. Soc. 2004, 126, pp. 15046-15047.
Frutos S., et al., "Access to site-specific Fc-cRGD peptide conjugates through streamlined expressed protein ligation", Org Biomol Chem., Oct. 12, 2016; 14 (40), 9549-9553.
Extended European Search Report dated Oct. 31, 2019 in European Patent Application No. 17792749.8, 9 pages.

\* cited by examiner 1 2 3 4

AZIDE GROUP-CONTAINING FC PROTEIN

CROSS REFERENCES TO RELATED APPLICATIONS

This application is a continuation of International Patent Application No. PCT/JP2017/017013, filed on Apr. 28, 2017, and claims priority to Japanese Patent Application No. 2016-092785, filed on May 2, 2016, both of which are incorporated herein by reference in their entireties.

BACKGROUND OF THE INVENTION

Field of the Invention

The present invention relates to azide group-containing Fc proteins and method of producing the same, and Fc protein derivatives added with a substance of interest using an azide group-containing Fc protein as a raw material and a method of producing the same, and the like.

Discussion of the Background

Since a substance of interest such as a protein has various physiological activities, a variety of preparations are developed by using such substance of interest. To improve the characteristics such as stability, a fusion protein of a substance of interest such as a protein and an Fc protein is developed.

U.S. Pat. No. 5,428,130, which is incorporated herein by reference in its entirety, describes a method of preparing a fusion protein of a protein of interest and an Fc protein based on a recombinant method.

U.S. Pat. No. 7,404,956, which is incorporated herein by reference in its entirety, describes a method of preparing a fusion protein ($R_1$—CO—NH—CH(CH$_2$SH)—$R_2$) of a peptide of interest and an Fc protein by reacting an Fc protein (NH$_2$—CH(CH$_2$SH)—$R_2$) having an N-terminal cysteine residue with thioester ($R_1$—CO—SR) of a peptide of interest based on a native chemical ligation method.

U.S. Pat. No. 7,737,260, which is incorporated herein by reference in its entirety, describes a method of preparing a fusion protein ($R_1$—CH$_2$—CH$_2$—NH—$R_2$) of a protein of interest and an Fc protein by reacting a peptide of interest having a formyl group ($R_1$—CH$_2$—CHO) with an Fc protein (H$_2$N—$R_2$) having an amino group based on a reductive amination reaction.

WO 2014/004639 A, which is incorporated herein by reference in its entirety, describes a method of preparing a fusion protein of a peptide of interest and an Fc protein by preparing an Fc protein introduced with an azide group at an arbitrary position in a cell-free protein expression system followed by Strain-promoted azide-alkyne cyclization (SPAAC) reaction.

The recombinant method described in U.S. Pat. No. 5,428,130 has a problem in terms of versatility since a fusion protein may not be expressed depending on the sequence of the fusion protein and the method cannot be employed when an Fc protein is required to be fused to a substance of interest other than protein.

The native chemical ligation method described in U.S. Pat. No. 7,404,956 has a problem in terms of the reaction efficiency and complexity of purification since even when an excessively large amount of thioester of a protein of interest is used, a mixture of mono-adduct and di-adduct of a protein of interest to an Fc protein is yielded.

The reductive amination reaction described in U.S. Pat. No. 7,737,260 has a problem in terms of the reaction efficiency, and has a problem that the sodium cyanoborohydride used in the reaction causes a side reaction which is a chemical conversion of a protein side chain.

The method described in WO 2014/004639 A has a problem that it cannot be recognized as a practically useful method in terms of the obtainability of a raw material of a cell-free protein expression system and costs.

Thus, there remains a need for improved methods of making fusion proteins of a substance of interest such as a protein, and an Fc protein.

SUMMARY OF THE INVENTION

Accordingly, it is one object of the present invention to provide novel means capable of efficiently producing a fused substance of an Fc protein and a substance of interest (for example, protein).

These and other objects, which will become apparent during the following detailed description, have been achieved by the inventors' discovery that, by manufacturing a certain azide group-containing Fc protein based on a specific enzymatic reaction and using the manufactured azide group-containing Fc protein as a raw material, a fusion protein of a protein of interest and an Fc protein can be produced with high efficiency, and the like. It is considered that the methodology developed by the inventors of the present invention, in which a certain azide group-containing Fc protein is used as a raw material, has excellent versatility since the method can be applied to addition of a substance other than protein to an Fc protein and also has an excellent practical value since use of a cell-free protein expression system can be avoided.

Thus, the present invention provides:

(1) An azide group-containing Fc protein represented by the following formula (1):

$$N_3\text{-}L_a\text{-}Phe\text{-}L_b\text{-}Fc \qquad (1)$$

wherein $N_3$ represents an azide group;

$L_a$ represents a bond or a divalent group;

Phe represents a residue of phenylalanine or a derivative thereof;

$L_b$ represents a lysine residue or an arginine residue, or a peptide linker consisting of two or more amino acid residues having a lysine residue or an arginine residue at/on the N-terminus; and Fc represents an Fc protein.

(2) The azide group-containing Fc protein according to (1), wherein the peptide linker consists of 4 to 30 amino acid residues.

(3) The azide group-containing Fc protein according to (2), wherein the peptide linker consists of 16 amino acid residues.

(4) The azide group-containing Fc protein according to any of (1) to (3), wherein the azide group-containing Fc protein represented by the formula (1) is represented by the following formula (1-1):

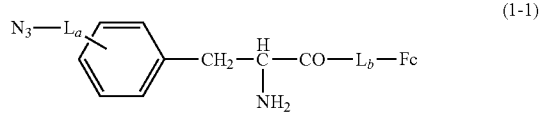

(1-1)

wherein $N_3$, $L_a$, $L_b$, and Fc are the same as in the formula (1); and the benzene ring may be further substituted.

(5) The azide group-containing Fc protein according to any of (1) to (4), wherein the Fc protein is derived from an Fc region of a mammalian antibody.

(6) The azide group-containing Fc protein according to (5), wherein the mammalian antibody is a human antibody.

(7) The azide group-containing Fc protein according to any of (1) to (6), wherein the Fc protein is derived from an Fc region of an IgG antibody.

(8) The azide group-containing Fc protein according to any of (1) to (7), wherein the Fc protein is selected from the group consisting of the following (a) to (c):

(a) a protein comprising the amino acid sequence of SEQ ID NO: 1;

(b) a protein comprising an amino acid sequence comprising one or several amino acid residue mutations selected from the group consisting of amino acid residue deletions, substitutions, additions, and insertions in the amino acid sequence of SEQ ID NO: 1; and (c) a protein comprising an amino acid sequence having at least 90% or more homology to the amino acid sequence of SEQ ID NO: 1.

(9) A method of producing an azide group-containing Fc protein, comprising reacting an azide group-containing phenylalanine derivative represented by the following formula (2):

$$N_3\text{-}L_a\text{-}Phe \quad (2)$$

wherein $N_3$ represents an azide group;

$L_a$ represents a bond or a divalent group; and

Phe represents phenylalanine or a derivative thereof;

with an Fc protein having a lysine residue or an arginine residue at/on the N-terminus represented by the following formula (3):

$$L_b\text{-}Fc \quad (3)$$

wherein $L_b$ represents a lysine residue or an arginine residue, or a peptide linker consisting of two or more amino acid residues having a lysine residue or an arginine residue at/on the N-terminus; and Fc represents an Fc protein;

by using phenylalanyl tRNA, aminoacyl tRNA synthetase, and leucyl/phenylalanyl tRNA transferase, to yield an azide group-containing Fc protein represented by the following formula (1):

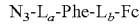
$$N_3\text{-}L_a\text{-}Phe\text{-}L_b\text{-}Fc \quad (1)$$

wherein $N_3$ and $L_a$ are the same as in the formula (2);

Phe represents a residue of phenylalanine or a derivative thereof; and $L_b$ and Fc are the same as in the formula (3).

(10) An Fc protein derivative fused with a substance of interest represented by the following formula (4):

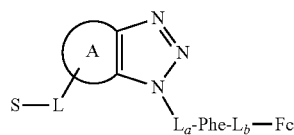

wherein S represents a substance of interest;
L represents a bond or a divalent group;
ring A represents a ring fused to triazole;

$L_a$ represents a bond or a divalent group;
Phe represents a residue of phenylalanine or a derivative thereof;
$L_b$ represents a lysine residue or an arginine residue, or a peptide linker consisting of two or more amino acid residues having a lysine residue or an arginine residue at/on the N-terminus; and
Fc represents an Fc protein.

(11) The Fc protein derivative according to (10), wherein the ring A is a 7- to 9-membered monocycle or a fused ring of a 7- to 9-membered monocycle and other ring.

(12) The Fc protein derivative according to (10) or (11), wherein the substance of interest is a polymeric substance.

(13) The Fc protein derivative according to any of (10) to (12), wherein the substance of interest is a peptide, a saccharide, or a nucleotide.

(14) The Fc protein derivative according to any of (10) to (13), wherein the substance of interest is a peptide having a cysteine residue at/on the C-terminus.

(15) A method of producing an Fc protein derivative fused with a substance of interest, comprising reacting a substance of interest derivatized with a ring having a triple bond between carbon atoms represented by the following formula (5):

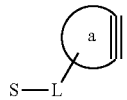

wherein S represents a substance of interest;
L represents a bond or a divalent group; and
ring a represents a ring having a triple bond between carbon atoms;
with an azide group-containing Fc protein represented by the following formula (1):

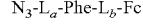
$$N_3\text{-}L_a\text{-}Phe\text{-}L_b\text{-}Fc \quad (1)$$

wherein $N_3$ represents an azide group;
$L_a$ represents a bond or a divalent group;
Phe represents a residue of phenylalanine or a derivative thereof;
$L_b$ represents a lysine residue or an arginine residue, or a peptide linker consisting of two or more amino acid residues having a lysine residue or an arginine residue at/on the N-terminus; and
Fc represents an Fc protein;
to yield an Fc protein derivative fused with a substance of interest represented by the following formula (4):

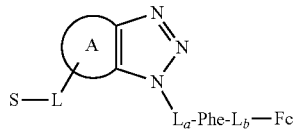

wherein S and L are the same as in the formula (5);
ring A represents a ring fused to triazole; and
$L_a$, Phe, $L_b$, and Fc are the same as in the formula (1).

(16) The method according to (15), wherein the ring having a triple bond between carbon atoms is a 7- to 9-membered ring or a fused ring of a 7- to 9-membered monocycle and another ring.

(17) The method according to (15) or (16), further comprising reacting the substance of interest with a reagent comprising a ring having a triple bond between carbon atoms to yield a substance of interest added with a ring having a triple bond between carbon atoms.

(18) A method of producing an Fc protein derivative fused with a substance of interest, comprising the following (A) and (B):

(A) reacting an azide group-containing phenylalanine derivative represented by the following formula (2):

wherein $N_3$ represents an azide group;
$L_a$ represents a bond or a divalent group; and
Phe represents phenylalanine or a derivative thereof;
with an Fc protein having a lysine residue or an arginine residue at/on the N-terminus represented by the following formula (3):

wherein $L_b$ represents a lysine residue or an arginine residue, or a peptide linker consisting of two or more amino acid residues having a lysine residue or an arginine residue at/on the N-terminus; and
Fc represents an Fc protein;
by using phenylalanyl tRNA, aminoacyl tRNA synthetase, and leucyl/phenylalanyl tRNA transferase,
to yield an azide group-containing Fc protein represented by the following formula (1):

wherein $N_3$ and $L_a$ are the same as in the formula (2);
Phe represents a residue of phenylalanine or a derivative thereof; and
$L_b$ and Fc are the same as in the formula (3); and
(B) reacting a substance of interest derivatized with a ring having a triple bond between carbon atoms represented by the following formula (5):

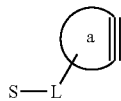

wherein S represents a substance of interest;
L represents a bond or a divalent group; and
ring a represents a ring having a triple bond between carbon atoms;
with the azide group-containing Fc protein represented by the above formula (1),
to yield an Fc protein derivative added with a substance of interest represented by the following formula (4):

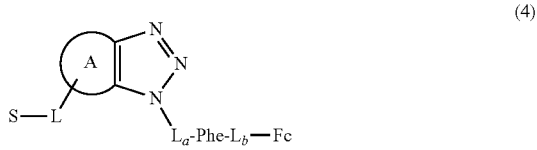

wherein S and L are the same as in the formula (5);
ring a represents a ring fused to triazole; and
$L_a$, Phe, $L_b$, and Fc are the same as in the formula (1).

(19) An Fc protein having a peptide linker consisting of 16 amino acid residues at/on the N-terminus.

(20) The Fc protein according to (19), wherein the N terminal amino acid residue of the peptide linker is a lysine residue or an arginine residue.

(21) An azide group-containing Fc protein having an azide group-containing phenylalanine derivative at/on the N-terminus of the azide group-containing Fc protein via a peptide linker consisting of 16 amino acid residues, wherein the N terminal amino acid residue of the peptide linker is a lysine residue or an arginine residue.

(22) A method of producing an azide group-containing Fc protein having an azide group-containing phenylalanine derivative at/on the N-terminus of the azide group-containing Fc protein via a peptide linker consisting of 16 amino acid residues, wherein the N terminal amino acid residue of the peptide linker is a lysine residue or an arginine residue,
said method comprising reacting an azide group-containing phenylalanine derivative with the Fc protein having the peptide linker at/on the N-terminus, by using phenylalanyl tRNA, aminoacyl tRNA synthetase, and leucyl/phenylalanyl tRNA transferase, to yield the azide group-containing Fc protein.

Effect of the Invention

Due to the excellent reaction efficiency with a substance of interest to be fused, the azide group-containing Fc protein of the present invention is useful for production of an Fc protein derivative added with a substance of interest. The present invention also provides an Fc protein derivative added with a substance of interest, which is produced by using the azide group-containing Fc protein, and the like.

The Fc protein of the present invention which has a peptide linker consisting of 16 amino acid residues at/on the N-terminus has excellent reaction efficiency with a substance of interest.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
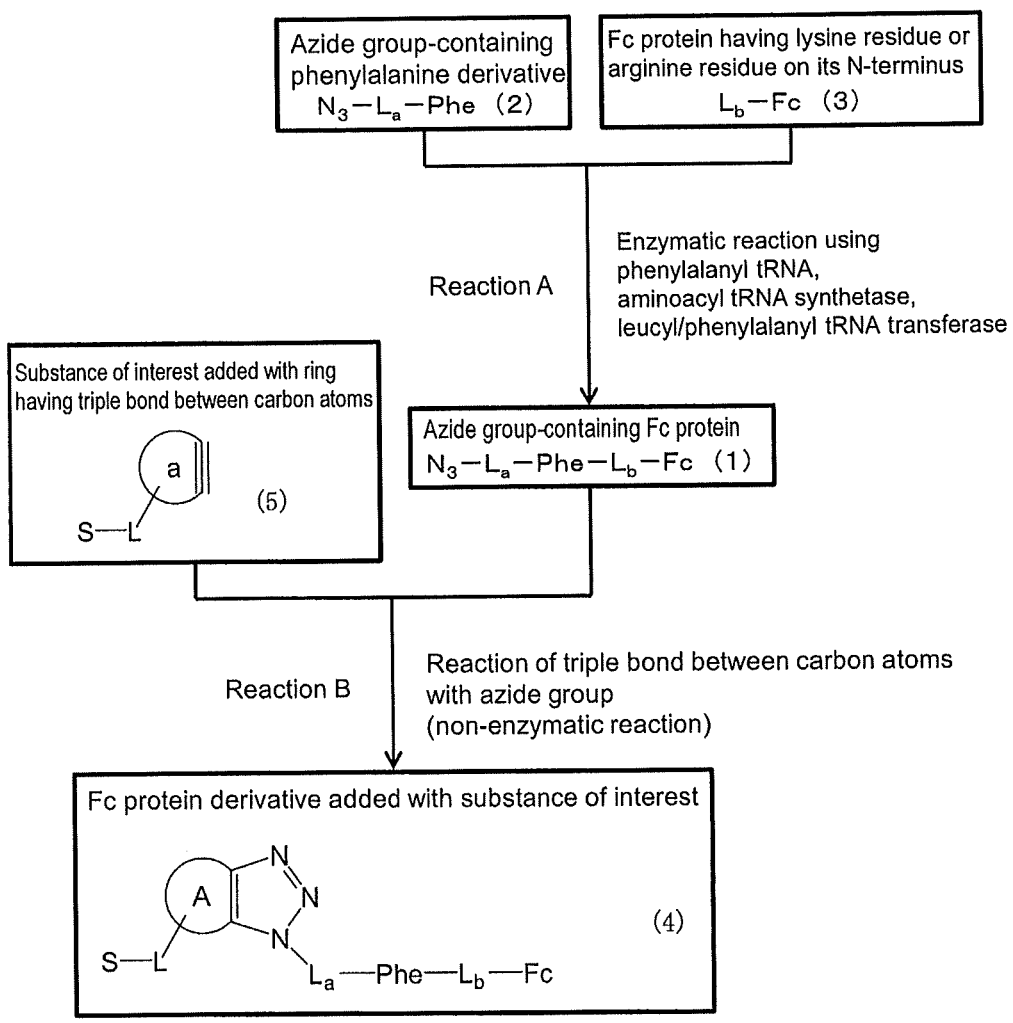
FIG. 1 is a drawing illustrating the outline of the present invention.

1. Azide Group-Containing Fc Protein and Method of Producing the Same

The present invention provides an azide group-containing Fc protein.

The azide group-containing Fc protein of the present invention is represented by the following formula (1).

$$N_3\text{-}L_a\text{-}Phe\text{-}L_b\text{-}Fc \quad (1)$$

wherein $N_3$ represents an azide group;

$L_a$ represents a bond or a divalent group;

Phe represents a residue of phenylalanine or a derivative thereof;

$L_b$ represents a lysine residue or an arginine residue, or a peptide linker consisting of two or more amino acid residues having a lysine residue or an arginine residue at/on the N-terminus; and Fc represents an Fc protein.

In formula (1), the bond between Phe and $L_b$ and the bond between $L_b$ and Fc are amide bonds. As such, the Phe-$L_b$-Fc portion of the above formula (1) represents a polypeptide structure in which the constitutional amino acid residues are linked via an amide bond.

In formula (1), the divalent group represented by $L_a$ is a group of linear chain or branched chain connecting $N_3$ and Phe. Examples of the divalent group represented by $L_a$ include a linear or branched divalent hydrocarbon group which may have a substituent, —C(=O)—, —C(=O)—O—, —NR$_a$— (R$_a$ represents a hydrogen atom or a substituent), —O—, —S—, —C(=O)—NR$_a$— (R$_a$ represents a hydrogen atom or a substituent), and the group consisting of combination of them.

Examples of the linear or branched divalent hydrocarbon group include alkylene, alkenylene, and alkynylene.

As for the alkylene, alkylene having carbon atom number of 1 to 12 is preferable, alkylene having carbon atom number of 1 to 6 is more preferable, and alkylene having carbon atom number of 1 to 4 is particularly preferable. The carbon atom number does not include carbon atom number of a substituent. The alkylene may be any of a linear chain, a branched chain, or a cyclic form, and is preferably linear alkylene. Examples of such alkylene include methylene, ethylene, propylene, butylene, pentylene, and hexylene.

As for the alkenylene, alkenylene having carbon atom number of 2 to 12 is preferable, alkenylene having carbon atom number of 2 to 6 is more preferable, and alkenylene having carbon atom number of 2 to 4 is particularly preferable. The carbon atom number does not include carbon atom number of a substituent. The alkenylene may be any of a linear chain, a branched chain, or a cyclic form, and is preferably linear alkenylene. Examples of such alkenylene include ethylenylene, propenylene, butenylene, pentenylene, and hexenylene.

As for the alkynylene, alkynylene having carbon atom number of 2 to 12 is preferable, alkynylene having carbon atom number of 2 to 6 is more preferable, and alkynylene having carbon atom number of 2 to 4 is particularly preferable. The carbon atom number does not include carbon atom number of a substituent. The alkynylene may be any of a linear chain, a branched chain, or a cyclic form, and is preferably linear alkynylene. Examples of such alkynylene include ethynylene, propynylene, butynylene, pentynylene, and hexynylene.

The substituent which the linear or branched divalent hydrocarbon group may have and the substituent represented by $R_a$ are substantially the same as the substituent which the phenylalanine derivative may have as described later, and the preferred ranges are also substantially the same. In particular, a hydrocarbon group is preferable. The number of the substituents which the linear or branched divalent hydrocarbon group may have is, for example, 1 to 5, and preferably 1 to 3, and more preferably 1 or 2.

Among them, as for the divalent group represented by $L_a$, a divalent hydrocarbon group is preferable, and alkylene is more preferable.

Particularly preferably, $L_a$ is a bond. In that case, the formula (1) may be represented as $N_3$-Phe-$L_b$-Fc (1').

In the formula (1), a residue of phenylalanine or a derivative thereof represented by Phe binds to the adjacent $L_b$ (a lysine residue or an arginine residue, or a lysine residue or an arginine residue at/on the N-terminus in a peptide linker) via an amide bond, and thus has the C terminal structure of amide bond (that is, CO—) at/on the C-terminus. The derivative of phenylalanine is a phenylalanine having 1 to 5, 1 to 3, or 1 or 2 substituents in the side chain moiety of phenylalanine (benzyl group). Examples of such substituents include the following:

(i) Hydrocarbon group, halogen atom (for example, fluorine atom, chlorine atom, bromine atom, iodine atom), guanidino, or cyano;

(ii) $R_b$—O—, $R_b$—C(=O)—, $R_b$—O—C(=O)—, or $R_b$—C(=O)—O—, wherein $R_b$ in (ii) represents a hydrogen atom or a hydrocarbon group; or (iii) $NR_{b1}R_{b2}$—, $NR_{b1}R_{b2}$—C(=O)—, $NR_{b1}R_{b2}$—C(=O)—O—, or $R_{b1}$—C(=O)—$NR_{b2}$—, wherein $R_{b1}$ and $R_{b2}$ in (iii), which are the same or different from each other, represent a hydrogen atom or a hydrocarbon group.

The hydrocarbon group in (i) to (iii) is a linear, branched, or cyclic monovalent hydrocarbon group, and is preferably a linear or branched monovalent hydrocarbon group. Examples of such hydrocarbon group include alkyl, alkenyl, and alkynyl.

As for the alkyl, for example, alkyl having carbon atom number of 1 to 12 is preferable, alkyl having carbon atom number of 1 to 6 is more preferable, and alkyl having carbon atom number of 1 to 4 is particularly preferable. The alkyl may be any of a linear chain, a branched chain, or a cyclic form, and is preferably linear or branched alkyl. Examples of such alkyl include methyl, ethyl, propyl, iso-propyl, butyl, iso-butyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl.

As for the alkenyl, alkenyl having carbon atom number of 2 to 12 is preferable, alkenyl having carbon atom number of 2 to 6 is more preferable, and alkenyl having carbon atom number of 2 to 4 is particularly preferable. The alkenyl may be any of a linear chain, a branched chain, or a cyclic form, and is preferably linear or branched alkenyl. Examples of such alkenyl include ethenyl, propenyl, butenyl, pentenyl, and hexenyl.

As for the alkynyl, alkynyl having carbon atom number of 2 to 12 is preferable, alkynyl having carbon atom number of 2 to 6 is more preferable, and alkynyl having carbon atom number of 2 to 4 is particularly preferable. The alkynyl may be any of a linear chain, a branched chain, or a cyclic form, and is preferably linear or branched alkynyl. Examples of such alkynyl include ethynyl, propynyl, butynyl, pentynyl, and hexynyl.

In the formula (1), $L_b$ represents a lysine residue or an arginine residue, or a peptide linker consisting of two or more amino acid residues having a lysine residue or an arginine residue at/on the N-terminus. The reason why $L_b$ is a lysine residue or an arginine residue, or a peptide linker having a lysine residue or an arginine residue at/on the N-terminus is that, with regard to a method of producing an azide group-containing Fc protein represented by the formula (1), for connecting the azide group-containing phenylalanine derivative (which may correspond to the structural unit of "$N_3$-$L_a$-Phe") to $L_b$ via an amide bond, it is necessary to use an arginine residue or a lysine residue as an amino acid to which the phenylalanine derivative can be connected. For details, reference can be made to the reaction using phenylalanyl tRNA, aminoacyl tRNA synthetase, and leucyl/phenylalanyl tRNA transferase for a method of producing an azide group-containing Fc protein represented by the formula (1) as described later.

Preferably, $L_b$ represents a peptide linker consisting of two or more amino acid residues having a lysine residue or an arginine residue at/on the N-terminus. The amino acid residue indicates a residue of L-amino acid or D-amino acid, and is preferably a residue of L-amino acid. Furthermore, an α-amino acid is preferred as the amino acid residue. More specifically, examples of a preferred amino acid residue include L-alanine (A), L-asparagine (N), L-cysteine (C), L-glutamine (Q), L-isoleucine (I), L-leucine (L), L-methionine (M), L-phenylalanine (F), L-proline (P), L-serine (S), L-threonine (T), L-tryptophan (W), L-tyrosine (Y), L-valine (V), L-aspartic acid (D), L-glutamic acid (E), L-arginine (R), L-histidine (H), or L-lysine (K), and glycine (G).

More preferably, the peptide linker consists of 4 or more amino acid residues. It is also possible that the peptide linker consists of 6 or more, 8 or more, 10 or more, 12 or more, or 14 or more amino acid residues. Furthermore, it is also possible that that the peptide linker consists of 30 or less, 25 or less, 20 or less, or 18 or less amino acid residues. Particularly preferably, the peptide linker consists of 16 amino acid residues.

According to a specific embodiment, the peptide linker may consist of an amino acid sequence heterogeneous to the amino acid sequence of an Fc protein. As for the peptide linker, an amino acid sequence "heterogeneous" to the amino acid sequence of an Fc protein means that it consists of an amino acid sequence that is different from the amino acid sequence in which the Fc protein is naturally connected in an antibody. In a natural antibody containing an Fc protein which consists of the amino acid sequence of SEQ ID NO: 1, for example, the N-terminal amino acid (methionine) residue of the Fc protein is naturally connected to the C-terminus of glycine, but when a protein consisting of the amino acid sequence of SEQ ID NO: 1 is used as an Fc protein, the peptide linker consists of an amino acid sequence which does not include a glycine residue at/on the C-terminus thereof.

According to a specific preferred embodiment, the peptide linker may be as follows:

(1) peptide consisting of the amino acid sequence of KVDKKVEPKSSDKTHT (SEQ ID NO: 8); or (2) peptide consisting of an amino acid sequence which includes a mutation of one or two amino acid residues selected from the group consisting of deletion, substitution, addition, and insertion of an amino acid residue in the amino acid sequence of KVDKKVEPKSSDKTHT (SEQ ID NO: 8).

The Fc protein represented by Fc in the formula (1) is derived from an Fc region in an antibody of any kind of an animal (for example, birds such as chickens and mammals). Preferably, the animal species from which the Fc protein originates are mammals. Examples of the mammals include primates (for example, human, monkey, and chimpanzee), rodents (for example, mouse, rat, guinea pig, and rabbit), cow, pig, horse, goat, and sheep. However, primates and rodents are preferable, primates are more preferable, and a human is still more preferable.

Examples of the antibody from which the Fc protein originates include IgG (for example, IgG1, IgG2, IgG3, and IgG4), IgM, IgA, IgD, IgE, and IgY, and an Fc part hybrid of those antibodies. It is preferably IgG, IgM, IgA, IgD, or IgE, and more preferably IgG.

Particularly preferably, the Fc protein is human IgG (for example, IgG1, IgG2, IgG3, or IgG4).

According to a specific embodiment, the Fc protein is selected from the group consisting of the following (a) to (c):

(a) a protein comprising the amino acid sequence of SEQ ID NO: 1;

(b) a protein comprising an amino acid sequence comprising one or several amino acid residue mutations selected from the group consisting of amino acid residue deletions, substitutions, additions, and insertions in the amino acid sequence of SEQ ID NO: 1; and (c) a protein comprising an amino acid sequence having at least 90% or more homology to the amino acid sequence of SEQ ID NO: 1.

With regard to the protein of above (b), number of the mutations on one or more amino acid residues is, for example, 1 to 50, preferably 1 to 40, more preferably 1 to 30, still more preferably 1 to 20, and most preferably 1 to 10 (for example, 1, 2, 3, 4, or 5).

With regard to the protein of above (c), the homology percent of an amino acid sequence may be preferably 92% or more, more preferably 95% or more, still more preferably 97% or more, and most preferably 98% or more, or 99% or more. Examples of homology include identity and similarity. Identity is more preferable.

Homology of amino acid sequence can be determined using algorithm BLAST by Karlin and Altschul (Pro. Natl. Acad. Sci., USA, 90, 5873 (1993) which is incorporated herein by reference inits entirety), and FASTA by Pearson (Methods Enzymol., 183, 63 (1990) which is incorporated herein by reference in its entirety). Since the program called BLASTP is developed based on this algorithm BLAST (see, http://www.ncbi.nlm.nih.gov), homology of amino acid sequence may be calculated using these programs with default setting. Also, for example, a numerical value obtained by calculating similarity as a percentage at a setting of "Unit size to compare=2" using the full length of a polypeptide portion encoded in ORF with the software GENETYX Ver. 7.0.9 from GENETYX CORPORATION employing Lipman-Pearson method may be used as homology of amino acid sequence. Alternatively, the homology may be a value (Identity) calculated using a parameter of default setting (Gap penalty=10, Extend penalty=0.5, Matrix=EBLOSUM62) in a NEEDLE program (J Mol Biol 1970; 48: 443-453, which is incorporated herein by reference in its entirety) search. The lowest value among the values derived from these calculations may be employed as the amino acid sequence homology. Preferably, the homology may be a value obtained by using the above parameters for NEEDLE program search.

A position of an amino acid residue at which a mutation can be introduced to the amino acid sequence of SEQ ID NO: 1 for preparing the proteins of above (b) and (c) would be obvious to a person skilled in the art, and, for example, a mutation can be introduced with reference to an alignment of amino acid sequences. Specifically, a person who is skilled in the art can 1) compare the amino acid sequences of multiple homologs, 2) identify clearly the regions that are relatively conserved and the regions that are not relatively conserved, and then 3) predict the regions capable of playing a functionally important role and the regions incapable of playing a functionally important role from the regions that are relatively conserved and the regions that are not relatively conserved, respectively, and thus can recognize a correlation between structure and function. As such, a person who is skilled in the art can suitably introduce a mutation of one or more amino acid residues such that the function of the Fc protein (for example, long half-life in circulating blood) is maintained.

For preparing the proteins of above (b) and (c), when an amino acid residue mutation is introduced into the amino acid sequence of SEQ ID NO: 1 and the amino acid residue mutation is a substitution, such a substitution of amino acid residue may be a conservative substitution. The term "conservative substitution" refers to a substitution of a certain amino acid residue with an amino acid residue having a similar side chain. Families of amino acid residues having similar side chains are well-known in the art. Examples of such families may include amino acids having a basic side chain (for example, lysine, arginine, histidine), amino acids having an acidic side chain (for example, aspartic acid, glutamic acid), amino acids having a non-charged polar side chain (for example, asparagine, glutamine, serine, threonine, tyrosine, cysteine), amino acids having a non-polar side chain (for example, glycine, alanine, valine, leucine, isoleucine, proline, phenylalanine, methionine, tryptophan), amino acids having a branched side chain at β position (for example, threonine, valine, isoleucine), amino acids having an aromatic side chain (for example, tyrosine, phenylalanine, tryptophan, histidine), amino acids having a hydroxyl group-containing (for example, alcoholic, phenolic) side chain (for example, serine, threonine, tyrosine), and amino acids having a sulfur-containing side chain (for example, cysteine, methionine). There is a case in which the amino acids having a non-charged polar side chain and amino acids having a non-polar side chain are comprehensively referred to as a neutral amino acid. Preferably, the conservative substitution of the amino acids may be the substitution between aspartic acid and glutamic acid, the substitution among arginine, lysine, and histidine, the substitution between tryptophan and phenylalanine, the substitution between phenylalanine and valine, the substitution among leucine, isoleucine, and alanine, and the substitution between glycine and alanine.

Preferably, the azide group-containing Fc protein represented by the above formula (1) is represented by the following formula (1-1).

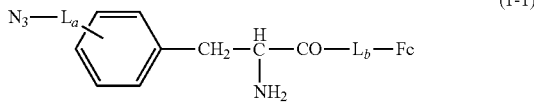

wherein $N_3$ represents an azide group;

$L_a$ represents a bond or a divalent group;

$L_b$ represents a lysine residue or an arginine residue, or a peptide linker consisting of two or more amino acid residues having a lysine residue or an arginine residue at/on the N-terminus;

Fc represents an Fc protein; and the benzene ring may be further substituted.

In the formula (1-1), the definitions, the examples, and the preferred examples of $L_a$, $L_b$, and Fc are the same as those of the formula (1).

In the formula (1-1), the benzene ring has a $N_3$-$L_a$-group at an arbitrary position, and preferably at the meta position or para position to the —$CH_2$—$CH(NH_2)$—CO-$L_b$-Fc group. When the benzene ring is substituted, the substituent is substantially the same as the substituent which the phenylalanine derivative may have as described above, and the preferred range is also substantially the same. The number of the substituents is 1 to 5, preferably 1 to 3, and more preferably 1 or 2.

More preferably, the benzene ring in the formula (1-1) has a $N_3$-$L_a$-group at the para position to the —$CH_2$—$CH(NH_2)$—CO-$L_b$-Fc group.

The present invention also provides a method of producing an azide group-containing Fc protein represented by the above formula (1). The method comprises reacting an azide group-containing phenylalanine derivative represented by the following formula (2) with an Fc protein having a lysine residue or an arginine residue at/on the N-terminus represented by the following formula (3), by using phenylalanyl tRNA, aminoacyl tRNA synthetase, and leucyl/phenylalanyl tRNA transferase, to yield an azide group-containing Fc protein represented by the above formula (1).

wherein $N_3$ represents an azide group;

$L_a$ represents a bond or a divalent group; and

Phe represents phenylalanine or a derivative thereof.

wherein $L_b$ represents a lysine residue or an arginine residue, or a peptide linker consisting of two or more amino acid residues having a lysine residue or an arginine residue at/on the N-terminus; and Fc represents an Fc protein.

In formula (2), the definitions, the examples, and the preferred examples of the divalent group represented by $L_a$ are the same as those of the formula (1).

In formula (2), the phenylalanine derivative represented by Phe is a phenylalanine having 1 to 5, 1 to 3, or 1 or 2 substituents in the side chain moiety of the phenylalanine (benzyl group). The substituent is substantially the same as the substituent which the phenylalanine derivative may have as described above, and the preferred range is also substantially the same. As for the azide group-containing phenylalanine derivative represented by the following formula (2), a significantly large number of derivatives are known. Accordingly, in the present invention, the derivative can be suitably synthesized or a commercially available product can be used.

Preferably, the azide group-containing phenylalanine derivative represented by the above formula (2) is represented by the following formula (2-1).

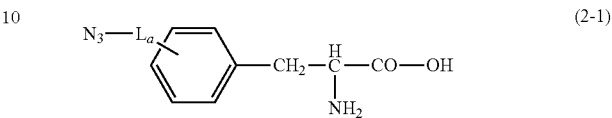

wherein $N_3$ represents an azide group;

$L_a$ represents a bond or a divalent group; and the benzene ring may be further substituted.

In formula (2-1), the definitions, the examples, and the preferred examples of the divalent group represented by $L_a$ are the same as those of the formula (1).

The benzene ring in the formula (2-1) has a $N_3$-$L_a$-group at an arbitrary position. However, it preferably has a $N_3$-$L_a$-group at the meta position or para position to the —$CH_2$—$CH(NH_2)$—COOH group. When the benzene ring is substituted, the substituent is substantially the same as the substituent which the phenylalanine derivative may have as described above, and the preferred range is also substantially the same. The number of the substituents is 1 to 5, preferably 1 to 3, and more preferably 1 or 2.

More preferably, the benzene ring in the formula (2-1) has a $N_3$-$L_a$-group at the para position to the —$CH_2$—CH($NH_2$)—COOH group.

In formula (3), the definitions, the examples, and the preferred examples of a peptide linker represented by $L_b$ are the same as those of the formula (1).

In formula (3), the definitions, the examples, and the preferred examples of the Fc protein represented by Fc are the same as those of the formula (1).

The Fc protein represented by the formula (3), which has a lysine residue or an arginine residue at/on the N-terminus, can be prepared by an arbitrary method. Examples of the method include (1) a method comprising expressing, in cultured cells, a protein in which a secretory signal peptide is added to a lysine residue or an arginine residue at/on the N-terminus of an Fc protein having a lysine residue or an arginine residue at/on the N-terminus, and recovering the Fc protein having a lysine residue or an arginine residue at/on the N-terminus from which the secretory signal peptide is cleaved off (see, WO 2002/081694 A; WO 2005/103278 A; and WO 2014/126260 A, all of which are incorporated herein by reference in their entireties, for example), (2) a method comprising adding a lysine residue or an arginine residue to the N terminal amino acid residue of an Fc protein (see, U.S. Pat. No. 7,404,956; and Proc. Jap. Acad. Ser. B, 2011, 603, both of which are incorporated herein by reference in their entireties, for example), and (3) a method of obtaining an Fc protein having a lysine residue or an arginine residue at/on the N-terminus by cleaving off, using a protease, a protein having a peptide added to the N terminal amino acid residue of an Fc protein.

According to the reaction using phenylalanyl tRNA, aminoacyl tRNA synthetase, and leucyl/phenylalanyl tRNA transferase (see, Reaction A of FIG. 1), phenylalanine or a derivative thereof can be added, via an amide bond, to a lysine residue or an arginine residue present at/on the N-terminus of a protein. This reaction is known as NEXT-A reaction (for example, JP 2009-106267 A, JP 2009-106268 A, and WO 2011/024887 A, all of which are incorporated herein by reference in their entireties).

The phenylalanyl tRNA (tRNA$^{Phe}$) can be prepared according to a previous report (for example, ChemBioChem 2009, 2460; and Nucleic Acids Res 1996, 907, both of which are incorporated herein by reference in their entireties). Alternatively, a commercially available product of tRNA$^{Phe}$ may be obtained.

The aminoacyl tRNA synthetase can be prepared according to a previous report (for example, ChemBioChem 2009, 2460; J. Am. Chem. Soc. 2002, 5652; BioChem 1991, 99; and ChemBioChem, 2002, 235-237, all of which are incorporated herein by reference in their entireties). As for the aminoacyl tRNA synthetase, the wild type aminoacyl tRNA synthetase which has a substrate specificity for phenylalanine or a derivative thereof, and a mutant of aminoacyl tRNA synthetase which has higher specificity for phenylalanine or a derivative thereof can be used. For example, phenylalanyl tRNA synthetase mutant originating from $E.$ $coli$ ($E.$ $coli$ PheRS) (for example, any one of Ala294→Gly mutant, Ala356→Trp mutant, Thr251→Ala mutant, and Gly318→Trp mutant, or a multiple mutant thereof) can be used. Alternatively, a commercially available product of aminoacyl tRNA synthetase may be obtained.

The leucyl/phenylalanyl tRNA transferase (L/F transferase) has an ability of transferring the phenylalanine or a derivative thereof bound to tRNA$^{Phe}$ to a protein which has a lysine residue or an arginine residue at/on the N-terminus. The leucyl/phenylalanyl tRNA transferase can be prepared according to a previous report (for example, ChemBioChem 2006, 1676; J. Biol. Chem. 1995, 20631; and ChemBioChem, 2008, 719-722, all of which are incorporated herein by reference in their entireties).

The reaction using phenylalanyl tRNA, aminoacyl tRNA synthetase, and leucyl/phenylalanyl tRNA transferase can be carried out in an aqueous medium such as suitable buffer containing co-enzyme (ATP), salts, or the like. Examples of the buffer include HEPES buffer and Tris-HCl. For example, the reaction can be carried out by using a mixture of MgCl$_2$, HEPES buffer containing spermidine, and a solution containing ATP.

The amounts of the azide group-containing phenylalanine derivative and the Fc protein having a lysine residue or an arginine residue at/on the N-terminus used for the reaction can be suitably set. For example, the azide group-containing phenylalanine derivative may be used in an amount of 1 to 5000 equivalents, preferably 1 to 500 equivalents, or more preferably 2 to 50 equivalents to the Fc protein having a lysine residue or an arginine residue at/on the N-terminus.

As for the reaction conditions such as reaction temperature, reaction pH, and reaction time, mild conditions free from protein denaturation can be suitably set. The reaction temperature is, for example, about 4° C. to 40° C., and preferably about 15° C. to 37° C. The reaction pH is, for example about 6 to 9, preferably about 6.5 to 8.5, and more preferably 7 to 8. The reaction time can be suitably set depending on the conditions of reaction temperature and reaction pH as well as the desired amount of substance to be yielded.

2. Fc Protein Derivative Added with Substance of Interest, and Method of Producing the Same The present invention also provides an Fc protein derivative added with a substance of interest.

The Fc protein derivative of the present invention is represented by the following formula (4).

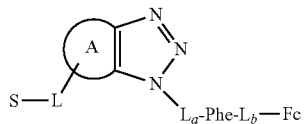

(4)

wherein S represents a substance of interest;
L represents a bond or a divalent group;
ring A represents a ring fused to triazole;
$L_a$ represents a bond or a divalent group;
Phe represents a residue of phenylalanine or a derivative thereof;
$L_b$ represents a lysine residue or an arginine residue, or a peptide linker consisting of two or more amino acid residues having a lysine residue or an arginine residue at/on the N-terminus; and
Fc represents an Fc protein.

In formula (4), the bond between Phe and $L_b$ and the bond between $L_b$ and Fc are amide bonds. As such, the Phe-$L_b$-Fc part of the above formula (4) indicates a polypeptide structure in which constitutional amino acid residues are linked to one another via an amide bond.

In formula (4), the substance of interest represented by S is a polymeric substance in which 2 or more constitutional units are connected to one another or a non-polymeric substance, and it is preferably a polymeric substance. The polymeric substance is a homopolymeric substance in which identical constitutional units are connected to one another or a heteropolymeric substance in which different constitutional units are connected to one another. The number of the constitutional units in the polymeric substance is not particularly limited as long as it is 2 or more. It is preferably 5 or more, 10 or more, 15 or more, 20 or more, 25 or more, or 30 or more. Furthermore, number of the constitutional units in the polymeric substance can be 500 or less, 300 or less, 200 or less, 100 or less, or 50 or less, for example. Examples of the polymeric substance include a peptide, a saccharide, and a nucleotide. Examples of the peptide that is used as a substance of interest in the present invention include an oligopeptide (for example, dipeptide, tripeptide, and tetrapeptide) and a polypeptide. The peptide may consist of the aforementioned 20 kinds of the L-α-amino acids and other arbitrary amino acids (for example, D-amino acid). The peptide may be linear, branched, or cyclic. The peptide may be modified with a molecule such as saccharide. Examples of the saccharide used as a substance of interest or for modification of a peptide in the present invention include oligosaccharide (for example, disaccharide, trisaccharide, and tetrasaccharide), and polysaccharide. Furthermore, the saccharide may be functional saccharide such as ligand. Examples of the nucleotide used as a substance of interest in the present invention include oligonucleotide (for example, dinucleotide, trinucleotide, and tetranucleotide), and polynucleotide. Examples of the nucleotide include natural nucleotide (for example, RNA and DNA), and non-natural nucleotide (for example, peptide nucleic acid, locked nucleic acid, cross-linked type nucleic acid, and phosphorothioate nucleic acid). The nucleotide may be a functional nucleotide such as antisense nucleic acid, RNA interference inducing nucleic acid (for example, siRNA), micro RNA (miRNA), or nucleic acid aptamer (for example, DNA aptamer and RNA aptamer). Furthermore, the substance of interest may be a pharmaceutical agent or a chemical reagent.

When the substance of interest is a peptide, a physiologically active polypeptide is preferred as a peptide. Examples of the physiologically active polypeptide include hormone, cytokine, chemokine, enzyme, antibody, proliferation factor, transcription regulation factor, vaccine, structure protein, ligand protein, receptor, cell surface antigen, receptor antagonist, blood factor, and peptide pharmaceuticals. More specific examples of the physiologically active polypeptide include human growth hormone, growth hormone releasing hormone, growth hormone releasing peptide, interferon, interferon receptor, colony stimulating factor, glucagon-like peptide (for example, GLP-1 (including precursor, and derivative such as mature form and intermediate, for example, JP 4548335 B2), Exenatide), G protein coupled receptor, interleukin, interleukin receptor, enzyme, interleukin binding protein, cytokine binding protein, macrophage activation factor, macrophage peptide, B cell factor, T cell factor, protein A, allergy inhibiting factor, cell necrosis glycoprotein, immune toxin, lymphotoxin, tumor necrosis factor, tumor inhibiting factor, transforming growth factor, α-1 antitrypsin, albumin, α-lactalbumin, apolypoprotein-E, erythropoietin, highly glycosylated erythropoietin, angiopoietins, hemoglobin, thrombin, thrombin receptor activating peptide, thrombomodulin, blood factor VII, VIIa, VIII, IX, and XIII, plasminogen activating factor, fibrin binding peptide, urokinase, streptokinase, hirudin, protein C, C-reactive protein, renin inhibitor, collagenase inhibitor, superoxide dismutase, leptin, platelet-derived growth factor, epidermal growth factor, epidermal growth factor, angiostatin, angiotensin, bone morphogenesis growth factor, bone morphogenesis promoting protein, calcitonin, insulin, atriopeptin, cartridge inducing factor, elcatonin, connective tissue activating factor, tissue factor pathway inhibitor, follicle stimulating hormone, luteinizing hormone, luteinizing hormone releasing hormone, nerve growth factors, parathyroid hormone, relaxin, secretin, somatomedin, insulin-like growth factor, adrenal cortex hormone, glucagon, cholecystokinin, pancreatic polypeptide, gastrin releasing peptide, adrenocorticotropic hormone releasing factor, thyroid stimulating hormone, autotaxin, lactoferrin, myostatin, receptors, receptor antagonist, cell surface antigen, monoclonal antibody, polyclonal antibody, and antibody fragment. As a fusion protein with an Fc protein, those physiologically active polypeptides can be suitably used (see, JP Patent No. 5020934 B2, which is incorporated herein by reference in its entirety, in particular). Preferred examples of the above glucagon-like peptide include Exenatide, GLP-1 (7-37), and GLP-1 (1-37) (JP Patent No. 4548335 B2, which is incorporated herein by reference in its entirety).

In formula (4), the divalent group represented by L is a linear, branched, or cyclic group, or a combination thereof, which connects the substance of interest S to the ring A. The divalent group represented by L may have a substituent. Examples of the divalent group represented by L include a divalent hydrocarbon group, —C(=O)—, —C(=O)—O—, —NR—(R represents a hydrogen atom or a substituent), —O—, —S—, —C(=O)—NR— (R represents a hydrogen atom or a substituent), a divalent heterocyclic group, and the group consisting of combination of two or more thereof (for example 2 to 8, preferably 2 to 6, and more preferably 2 to 4). L binds to any atom of the ring A, for example, a ring-constituting atom. Preferably, it binds to a ring-constituting atom other than the carbon atom shared by triazole.

The divalent hydrocarbon group is a linear, branched, or cyclic divalent hydrocarbon group, and is preferably a linear or branched divalent hydrocarbon group. Examples of the divalent hydrocarbon group include alkylene, alkenylene, alkynylene, and arylene.

The definitions, the examples, and the preferred examples of alkylene, alkenylene, and alkynylene as an example of the divalent group represented by L are the same as alkylene, alkenylene, and alkynylene as an example of the divalent group represented by $L_a$.

As for the arylene, arylene having carbon atom number of 6 to 24 is preferable, arylene having carbon atom number of 6 to 18 is more preferable, arylene having carbon atom number of 6 to 14 is further preferable, and arylene having carbon atom number of 6 to 10 is still more preferable. The carbon atom number does not include carbon atom number of a substituent. Examples of the arylene include phenylene (for example, a case in which the Fc protein derivative represented by the formula (4) is produced by using a fluorobenzene reagent), naphthylene, and anthracenylene.

The substituent represented by R in —NR— and —C(=O)—NR—, which is an example of the divalent group represented by L, is substantially the same as the substituent which the phenylalanine derivative may have as described above, and the preferred range is also substantially the same.

The divalent heterocyclic group as an example of the divalent group represented by L is either a divalent aromatic heterocyclic group or a divalent non-aromatic heterocyclic group. As a heteroatom for constituting the heterocycle, it is preferable to contain one or more kinds selected from the group consisting of oxygen atom, sulfur atom, nitrogen atom, phosphorus atom, boron atom, and silicon atom. It is more preferable to contain one or more kinds selected from the group consisting of oxygen atom, sulfur atom, and nitrogen atom.

As for the divalent aromatic heterocyclic group, a divalent aromatic heterocyclic group having carbon atom number of 3 to 21 is preferable, a divalent aromatic heterocyclic group having carbon atom number of 3 to 15 is more preferable, a divalent aromatic heterocyclic group having carbon atom number of 3 to 9 is further preferable, and a divalent aromatic heterocyclic group having carbon atom number of 3 to 6 is still more preferable. The carbon atom number does not include carbon atom number of a substituent. More specific examples of the divalent aromatic heterocyclic group include pyrenediyl, pyrroldiyl, furandiyl, thiophenediyl, pyridinediyl, pyridazinediyl, pyrimidinediyl, pyrazinediyl, triazinediyl, pyrrolinediyl, piperidinediyl, triazolediyl, purinediyl, anthraquinonediyl, carbazolediyl, fluorenediyl, quinolinediyl, and isoquinolinediyl.

As for the divalent non-aromatic heterocyclic group, a non-aromatic heterocyclic group having carbon atom number of 3 to 21 is preferable, a non-aromatic heterocyclic group having carbon atom number of 3 to 15 is more preferable, a non-aromatic heterocyclic group having carbon atom number of 3 to 9 is further preferable, and a non-aromatic heterocyclic group having carbon atom number of 3 to 6 is still more preferable. The carbon atom number does not include carbon atom number of a substituent. More specific examples of the divalent non-aromatic heterocyclic group include 2,5-pyrroldionediyl (in the case of producing the Fc protein derivative represented by the formula (4) by using a maleimide reagent), 3-pyrroline-2,5-dione-1,3-diyl (in the case of producing the Fc protein derivative by using a halogenated maleimide reagent), pyrrol-3-arylthio-2,5-dione-1,3-diyl (in the case of producing the Fc protein derivative by using an arylthiomaleimide reagent), oxiranediyl, aziridinediyl, azetidinediyl, oxetanediyl, thietanediyl, pyrrolidinediyl, dihydrofurandiyl, tetrahydrofurandiyl, dioxolanediyl, tetrahydrothiophenediyl, imidazolidinediyl, oxazolidinediyl, piperidinediyl group, dihydropyrandiyl, tetrahydropyrandiyl, tetrahydrothiopyrandiyl, morpholinediyl, thiomorpholinediyl, piperazinediyl, dihydrooxazinediyl, tetrahydrooxazinediyl, dihydropyrimidinediyl, and tetrahydropyrimidinediyl.

Preferred examples of divalent non-aromatic heterocyclic group include 2,5-pyrroldionediyl, 3-pyrroline-2,5-dione-1,3-diyl, and pyrrol-3-arylthio-2,5-dione-1,3-diyl.

Preferably, the divalent group represented by L is -$L_1$-$L_2$- ($L_1$ and $L_2$ represent a divalent group).

Here, the examples of the divalent group represented by $L_1$ include the divalent group described above for L. Preferably, it is arylene or a divalent heterocyclic group. More preferably, it is arylene or a divalent non-aromatic heterocyclic group. Still more preferably, it is phenyldiyl, 2,5-pyrroldionediyl, 3-pyrroline-2,5-dione-1,3-diyl, or pyrrol-3-arylthio-2,5-dione-1,3-diyl.

Examples of the divalent group represented by $L_2$ includes a divalent hydrocarbon group, —C(=O)—, —C(=O)—O—, —NR— (R represents a hydrogen atom or a substituent), —O—, —S—, —C(=O)—NR—(R represents a hydrogen atom or a substituent), a divalent heterocyclic group, or the group consisting of combination of two or more thereof (for example 2 to 7, preferably 2 to 5, and more preferably 2 or 3). Herein, the definitions, the examples, and the preferred examples of the divalent hydrocarbon group, —NR— (R represents a hydrogen atom or a substituent), —C(=O)—NR— (R represents a hydrogen atom or a substituent), and the divalent heterocyclic group as an example of the divalent group represented by $L_2$ are the same as those of the divalent group represented by L.

The divalent group represented by L, or $L_1$ or $L_2$ may have a substituent. The substituent is substantially the same as the substituent which the phenylalanine derivative may have as described above, and the preferred range is also substantially the same. The number of the substituents is 1 to 5, preferably 1 to 3, and more preferably 1 or 2.

In the formula (4), the ring A represents a ring fused to triazole. The constitutional part of the ring A does not include the fused triazole ring itself but includes the double bond part between carbon atoms shared with the triazole. As such, it can be said that the ring A is a ring having a double bond between carbon atoms.

The ring A is a monocycle or a fused ring of a monocycle and other ring. The ring A may have a substituent. As for the monocycle, a homocycle, or a heterocycle containing one or more selected from the group consisting of oxygen atom, sulfur atom, nitrogen atom, phosphorus atom, boron atom, and silicon atom is preferable. More preferably, the monocycle is a homocycle or a heterocycle containing one or more selected from a group consisting of oxygen atom, sulfur atom, and nitrogen atom. As for the monocycle, a 5- to 12-membered monocycle is preferable, a 6- to 10-membered monocycle is more preferable, and a 7- to 9-membered monocycle is still more preferable. As for the monocycle, a non-aromatic monocycle is preferable.

When the ring A is a fused ring, examples of other ring to be fused to a monocycle include cycloalkane, arene, and a heterocycle.

As for the cycloalkane, cycloalkane having carbon atom number of 3 to 24 is preferable, cycloalkane having carbon atom number of 6 to 18 is more preferable, cycloalkane having carbon atom number of 3 to 14 is even more preferable, and cycloalkane having carbon atom number of 3 to 10 is still even more preferable. The carbon atom number does not include carbon atom number of a substituent. Examples of the cycloalkane include cyclopropane, cyclobutane, cyclopentane, cyclohexane, cycloheptane, and cyclooctane.

As for the arene, arene having carbon atom number of 6 to 24 is preferable, arene having carbon atom number of 6 to 18 is more preferable, arene having carbon atom number of 6 to 14 is even more preferable, and arene having carbon atom number of 6 to 10 is still even more preferable. The carbon atom number does not include carbon atom number of a substituent. Examples of the arene include benzene, naphthalene, and anthracene.

The heterocycle is either an aromatic heterocycle or a non-aromatic heterocycle. As for the hetero atom constituting the heterocycle, it is preferable to contain one or more selected from the group consisting of oxygen atom, sulfur atom, nitrogen atom, phosphorus atom, boron atom, and silicon atom, and it is more preferable to contain one or more selected from the group consisting of oxygen atom, sulfur atom, and nitrogen atom.

As for the aromatic heterocycle, an aromatic heterocycle having carbon atom number of 3 to 21 is preferable, an aromatic heterocycle having carbon atom number of 3 to 15 is more preferable, an aromatic heterocycle having carbon atom number of 3 to 9 is even more preferable, and an aromatic heterocycle having carbon atom number of 3 to 6 is still even more preferable. The carbon atom number does not include carbon atom number of a substituent. More specifically, examples of the aromatic heterocycle include pyrene, pyrrole, furan, thiophene, pyridine, pyridazine, pyrimidine, pyrazine, triazine, pyrroline, piperidine, triazole, purine, anthraquinone, carbazole, fluorene, quinoline, and isoquinoline.

As for the non-aromatic heterocycle, a non-aromatic heterocycle having carbon atom number of 3 to 21 is preferable, a non-aromatic heterocycle having carbon atom number of 3 to 15 is more preferable, a non-aromatic heterocycle having carbon atom number of 3 to 9 is even more preferable, and a non-aromatic heterocycle having carbon atom number of 3 to 6 is still even more preferable. The carbon atom number does not include carbon atom number of a substituent. More specifically, examples of the non-aromatic heterocycle include oxirane, aziridine, azetidine, oxetane, thietane, pyrrolidine, dihydrofuran, tetrahydrofuran, dioxolane, tetrahydrothiophene, imidazolidine, oxazolidine, piperidine, dihydropyran, tetrahydropyran, tetrahydrothiopyran, morpholine, thiomorpholine, piperazine, dihydrooxazine, tetrahydrooxazine, dihydropyrimidine, and tetrahydropyrimidine.

The substituent which the ring A may have is substantially the same as the substituent which the phenylalanine derivative may have as described above, and the preferred range is also substantially the same. The number of the substituents is 1 to 5, for example. It is preferably 1 to 3, and more preferably 1 or 2.

Preferably, the ring A is a 7- to 9-membered monocycle or a fused ring of a 7- to 9-membered monocycle and other ring. Preferred examples of the ring A are as described below (for example, see Org. Biomol. Chem. 2013, 11, 6439 and Angew. Chem. Int. Ed. 2015, 54, 1190, which are incorporated herein by reference in their entireties).

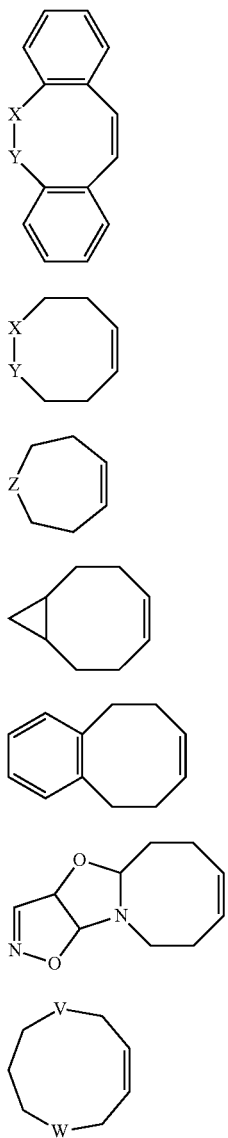

(i')

(ii')

(iii')

(iv')

(v')

(vi')

(vii')

wherein one of X and Y represents CH$_2$ and the other represents CH$_2$, NH, O, or S;

Z represents CH$_2$, NH, O, or S; and

V and W, which are the same or different from each other, represent CH$_2$, NH, O, or S.

In formula (4), the definitions, the examples, and the preferred examples of $L_a$, $L_b$, and Fc are the same as those of the above formula (1).

In formula (4), the definitions, the examples, and the preferred examples of Phe are the same as those of the above formula (1). Accordingly, the examples and preferred examples of the substituent which the phenylalanine derivative has are also the same as those described above. The number of the substituents is 1 to 5, preferably 1 to 3, and more preferably 1 or 2.

Preferably, the Fc protein derivative represented by the above formula (4) is represented by the following formula (4-1).

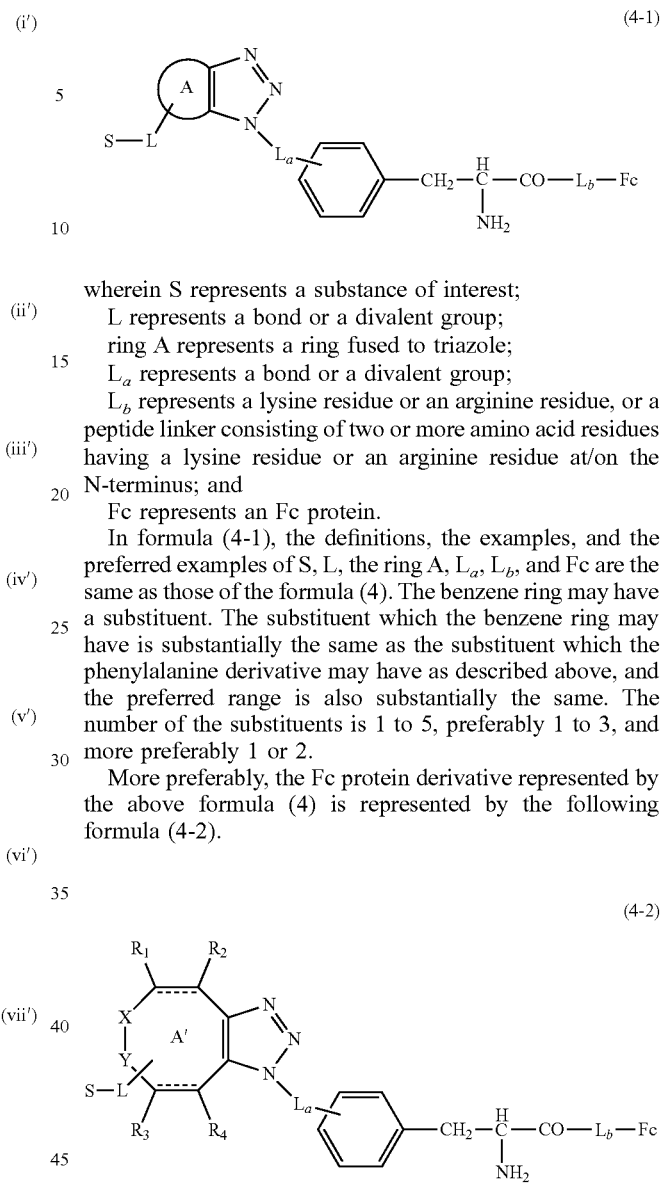

wherein S represents a substance of interest;

L represents a bond or a divalent group;

ring A represents a ring fused to triazole;

$L_a$ represents a bond or a divalent group;

$L_b$ represents a lysine residue or an arginine residue, or a peptide linker consisting of two or more amino acid residues having a lysine residue or an arginine residue at/on the N-terminus; and Fc represents an Fc protein.

In formula (4-1), the definitions, the examples, and the preferred examples of S, L, the ring A, $L_a$, $L_b$, and Fc are the same as those of the formula (4). The benzene ring may have a substituent. The substituent which the benzene ring may have is substantially the same as the substituent which the phenylalanine derivative may have as described above, and the preferred range is also substantially the same. The number of the substituents is 1 to 5, preferably 1 to 3, and more preferably 1 or 2.

More preferably, the Fc protein derivative represented by the above formula (4) is represented by the following formula (4-2).

wherein S represents a substance of interest;

L represents a bond or a divalent group;

ring A' represents a 8-membered ring fused to triazole;

one of X and Y represents CH$_2$ and the other represents CH$_2$, NH, O, or S;

$R_1$ to $R_4$, which are the same or different from one another, represent a hydrogen atom or a substituent; or alternatively, $R_1$ and $R_2$ may together form a ring having a substituent, $R_3$ and $R_4$ may together form a ring having a substituent;

double lines consisting of a solid line and a broken line in the ring A' represent a single bond or a double bond;

$L_a$ represents a bond or a divalent group;

$L_b$ represents a lysine residue or an arginine residue, or a peptide linker consisting of two or more amino acid residues having a lysine residue or an arginine residue at/on the N-terminus; and Fc represents an Fc protein.

In formula (4-2), the definitions, the examples, and the preferred examples of S, L, $L_a$, $L_b$, and Fc are the same as those of the formula (4). The benzene ring may have a substituent. The substituent which the benzene ring may have is substantially the same as the substituent which the phenylalanine derivative may have as described above, and the preferred range is also substantially the same. The number of the substituents is 1 to 5, preferably 1 to 3, and more preferably 1 or 2.

In the ring A', one of X and Y represents $CH_2$ and the other represents $CH_2$, NH, O, or S. Preferably, one of X and Y represents $CH_2$ and the other represents $CH_2$ or NH.

Preferably, X or Y is linked to L. In this case, the S-L-group which binds to the ring A' may be linked to X or Y to represent the structure of S-L-CH or S-L-N.

The substituents represented by $R_1$ to $R_4$ are substantially the same as the substituents which the phenylalanine derivative may have as described above, and the preferred ranges are also substantially the same.

Examples of the ring which may be formed by $R_1$ and $R_2$ together and/or $R_3$ and $R_4$ together include the cycloalkane, the arene, and the heterocycle which are described above. The definitions, the examples, and the preferred examples of the cycloalkane, the arene, and the heterocycle are the same as those described above. The substituents which the ring formed by $R_1$ and $R_2$ together and/or $R_3$ and $R_4$ together may have are substantially the same as the substituent which the phenylalanine derivative may have as described above, and the preferred range is also substantially the same. The number of the substituents is 1 to 5, preferably 1 to 3, and more preferably 1 or 2.

The ring A' may have, in addition to $R_1$ to $R_4$, an additional substituent. Such an additional substituent is substantially the same as the substituent which the phenylalanine derivative may have as described above, and the preferred range is also substantially the same. The number of the additional substituents is 1 to 5, preferably 1 to 3, and more preferably 1 or 2.

The present invention also provides a method of producing an Fc protein derivative represented by the above formula (4). The method comprises reacting a substance of interest added with a ring having a triple bond between carbon atoms represented by the following formula (5) with an azide group-containing Fc protein represented by the above formula (1) to yield an Fc protein derivative represented by the above formula (4).

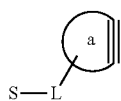

(5)

wherein S represents a substance of interest;
L represents a bond or a divalent group; and
ring a represents a ring having a triple bond between carbon atoms.

In formula (5), the definitions, the examples, and the preferred examples of S and L are the same as those of the above formula (4).

The ring a represents a ring having a triple bond between carbon atoms. The ring a is a monocycle or a fused ring of a monocycle and other ring. The ring a may have a substituent. As for the monocycle, a homocycle, or a heterocycle containing one or more selected from the group consisting of oxygen atom, sulfur atom, nitrogen atom, phosphorus atom, boron atom, and silicon atom is preferable. More preferably, the monocycle is a homocycle or a heterocycle containing one or more selected from the group consisting of oxygen atom, sulfur atom, and nitrogen atom. As for the monocycle, a 7- to 10-membered monocycle is preferable, and a 7- to 9-membered monocycle is more preferable. As for the monocycle, a non-aromatic monocycle is preferable.

When the ring a is a fused ring, examples of other ring to be fused to a monocycle include cycloalkane, arene, and a heterocycle. The definitions, the examples, and the preferred examples of cycloalkane, arene, and a heterocycle are the same as those of the other ring of a fused ring related to the ring A.

The substituent which the ring a may have is substantially the same as the substituent which the phenylalanine derivative may have as described above, and the preferred range is also substantially the same. The number of the substituents is, for example, 1 to 5 and is preferably 1 to 3, and more preferably 1 or 2.

Preferably, the ring a is a 7- to 9-membered monocycle or a fused ring of a 7- to 9-membered monocycle and other ring. Preferred examples of the ring a are as described below (for example, Org. Biomol. Chem. 2013, 11, 6439; Angew. Chem. Int. Ed. 2015, 54, 1190; J. Am. Chem. Soc. 2004, 126, 15046; J. Am. Chem. Soc. 2008, 130, 11486; and Chem. Commun. 2010, 46, 97, all of which are incorporated herein by reference in their entireties).

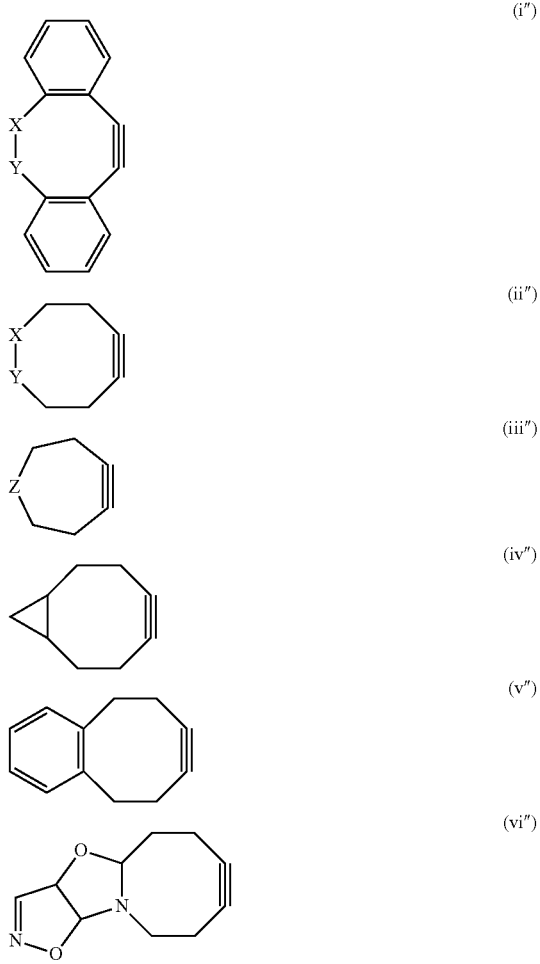

-continued

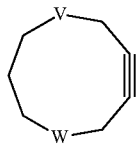
(vii″)

wherein one of X and Y represents $CH_2$ and the other represents $CH_2$, NH, O, or S;

Z represents $CH_2$, NH, O, or S; and

V and W, which are the same or different from each other, represent $CH_2$, NH, O, or S.

Preferably, the substance of interest added with a ring having a triple bond between carbon atoms as represented by the above formula (5) is a substance of interest added with a 8-membered ring having a triple bond between carbon atoms as represented by the following formula (5').

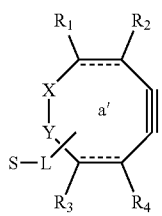
(5')

wherein S represents a substance of interest;

L represents a bond or a divalent group;

ring a' represents a 8-membered ring having a triple bond between carbon atoms;

one of X and Y represents $CH_2$ and the other represents $CH_2$, NH, O, or S;

$R_1$ to $R_4$, which are the same or different from one another, represent a hydrogen atom or a substituent; or alternatively, $R_1$ and $R_2$ may together form a ring having a substituent, $R_3$ and $R_4$ may together form a ring having a substituent; and double lines consisting of a solid line and a broken line in the ring A' represent a single bond or a double bond.

In formula (5'), the definitions, the examples, and the preferred examples of S, L, X, Y, and $R_1$ to $R_4$ are the same as those of the formula (4-2).

The ring a' may have, in addition to $R_1$ to $R_4$, an additional substituent. The additional substituent is substantially the same as the substituent which the phenylalanine derivative may have as described above, and the preferred range is also substantially the same. The number of the additional substituents is 1 to 5, preferably 1 to 3, and more preferably 1 or 2.

The reaction in the method of producing an Fc protein derivative can be carried out by allowing the substance of interest added with a ring having a triple bond between carbon atoms and the azide group-containing Fc protein to be co-present (see, Reaction B in FIG. 1). This is because the triple bond between carbon atoms in a certain ring and the azide group undergo a non-enzymatic reaction. Such a reaction can be carried out in the presence or absence of a copper catalyst. Such a reaction is also known as Huisgen reaction. The copper catalyst is used for increasing the reaction efficiency. However, from the viewpoint of avoiding cell cytotoxicity of a copper catalyst or remaining of a copper catalyst in the product, the reaction is preferably carried out in the absence of a copper catalyst. When a 7- to 9-membered monocycle or a fused ring of a 7- to 9-membered monocycle and other ring is used as the ring a, the reaction can be efficiently carried out in the absence of a copper catalyst. This reaction is also known as Strain-promoted azide-alkyne cyclization (SPAAC) reaction (for example, Org. Biomol. Chem. 2013, 11, 6439; Angew. Chem. Int. Ed. 2015, 54, 1190; J. Am. Chem. Soc. 2004, 126, 15046; J. Am. Chem. Soc. 2008, 130, 11486; and Chem. Commun. 2010, 46, 97, all of which are incorporated herein by reference in their entireties). In the present invention, extremely high reaction efficiency is confirmed even in the absence of a copper catalyst (see, the Examples, for example).

The method of producing an Fc protein derivative may further include reacting a substance of interest with a reagent which includes a ring having a triple bond between carbon atoms to yield a substance of interest that is added with a ring having a triple bond between carbon atoms. Examples of the reagent include a maleimide reagent, a halogenated maleimide reagent, an alkylthiomaleimide reagent, and a fluorobenzene reagent.

Amount of the substance of interest added with a ring having a triple bond between carbon atoms and an azide group-containing Fc protein, which are used for the reaction, can be suitably set. The substance of interest added with a ring having a triple bond between carbon atoms can be used in an amount of, for example, 1 to 100 equivalents, preferably 1 to 20 equivalents, more preferably 1.5 to 10 equivalents, and even more preferably 2 to 5 equivalents relative to an azide group-containing Fc protein.

The reaction can be carried out in an aqueous medium such as a suitable buffer solution. Examples of the buffer solution include phosphate buffer solution, HEPES buffer solution, and Tris-HCl.

As for the reaction conditions such as reaction temperature, reaction pH, and reaction time, mild conditions free from protein denaturation can be suitably set. The reaction temperature is, for example, about 4° C. to 40° C., and preferably about 15° C. to 37° C. The reaction pH is, for example about 6 to 9, preferably about 6.5 to 8.5, and more preferably 7 to 8. The reaction time can be suitably set depending on the conditions of reaction temperature and reaction pH as well as the desired amount of substance to be yielded.

The present invention also provides a method of producing an Fc protein derivative comprising the following steps:

(A) reacting an azide group-containing phenylalanine derivative with an Fc protein having a lysine residue or an arginine residue at/on the N-terminus by using phenylalanyl tRNA, aminoacyl tRNA synthetase, and leucyl/phenylalanyl tRNA transferase, to yield an azide group-containing Fc protein; and (B) reacting a substance of interest added with a ring having a triple bond between carbon atoms with the azide group-containing Fc protein, to yield an Fc protein derivative.

Step (A) can be carried out in the same manner as the method of producing an azide group-containing Fc protein according to the present invention (see, Reaction A in FIG. 1). The definitions, the examples, and the preferred examples of the phenylalanyl tRNA, aminoacyl tRNA synthetase, leucyl/phenylalanyl tRNA transferase, azide group-containing phenylalanine derivative, Fc protein having a lysine residue or an arginine residue at/on the N-terminus, and azide group-containing Fc protein of the step (A) are the same as those described before.

Step (B) can be carried out in the same manner as the method of producing an Fc protein derivative according to the present invention (see, Reaction B of FIG. 1). The definitions, the examples, and the preferred examples of the substance of interest added with a ring having a triple bond between carbon atoms, azide group-containing Fc protein, and Fc protein derivative of step (B) are the same as those described before.

Step (A) and step (B) can be carried out separately. Alternatively, step (A) and step (B) can be carried out simultaneously. That is because, the reactions of step (A) and step (B) are common in that they can be carried out in an aqueous medium at mild conditions free from protein denaturation. Accordingly, the method of the present invention comprising step (A) and step (B) may be carried out as a one-pot reaction.

The Fc protein derivative of the present invention is useful as a pharmaceutical agent or a chemical reagent, for example. Accordingly, the Fc protein derivative of the present invention may be provided in the form of a pharmaceutical composition. The pharmaceutical composition may comprise a pharmaceutically acceptable carrier in addition to the Fc protein derivative of the present invention. Examples of the pharmaceutically acceptable carrier include, but are not limited thereto, excipients such as sucrose, starch, mannitol, sorbitol, lactose, glucose, cellulose, talc, calcium phosphate, calcium carbonate, binders such as cellulose, methylcellulose, hydroxypropyl cellulose, polypropylpyrrolidone, gelatin, gum arabic, polyethylene glycol, sucrose, starch, disintegrants such as starch, carboxymethyl cellulose, hydroxypropyl starch, sodium hydrogen carbonate, calcium phosphate, calcium citrate, lubricants such as magnesium stearate, aerosil, talc, sodium lauryl sulfate, aromatics such as citric acid, menthol, glycyllysin•ammonium salt, glycine, orange powder, preservatives such as sodium benzoate, sodium bisulfate, methylparaben, propylparaben, stabilizing agents such as citric acid, sodium citrate, acetic acid, suspending agents such as methylcellulose, polyvinyl pyrrolidone, aluminum stearate, dispersing agents such as surfactant, diluents such as water, physiological saline, orange juice, base wax such as cacao butter, polyethylene glycol, white kerosene. Furthermore, from the viewpoint that the Fc protein derivative of the present invention has an Fc protein part, it can have higher stability in a living body of an animal such as human. The Fc protein derivative of the present invention may have, in addition to the fusion to an Fc protein, any new modification for achieving stabilization (for example, PEGylation).

Examples of a preparation that is suitable for oral administration include a liquid preparation having an effective amount of an effective ingredient dissolved in a diluent such as water, physiological saline, or orange juice, a capsule, a sachet, or a tablet containing an effective amount of an effective ingredient as a solid or a granule, a suspension having an effective amount of an effective ingredient suspended in a suitable dispersion medium, and an emulsion having a solution in which an effective amount of an effective ingredient is dissolved and which is emulsified by dispersion in a suitable dispersion medium.

The pharmaceutical composition of the present invention is suitable for parenteral administration (for example, intravenous injection, subcutaneous injection, muscle injection, topical application, and intraperitoneal administration). Examples of a pharmaceutical composition that is suitable for parenteral administration include an aqueous or non-aqueous and isotonic sterile injection solution, in which an anti-oxidant, a buffer, a bactericidal agent, an isotonic agent, or the like may be contained. Further examples include an aqueous or non-aqueous sterile suspension, in which a suspending agent, a solubilizing agent, a thickening agent, a stabilizer, a preservative, or the like may be contained.

Dosage of the pharmaceutical composition of the present invention can be suitably set although it may vary depending on the type and activity of an effective ingredient, severeness of a disease, animal type as an administration subject, and pharmaceutical compliance, body weight, age, or the like of an administration subject.

3. Fc Protein Having Peptide Linker Consisting of 16 Amino Acid Residues

The present invention provides an Fc protein which has a peptide linker consisting of 16 amino acid residues at/on the N-terminus.

The definitions, the examples, and the preferred examples of the peptide linker are the same as those described in the above section of (1. Azide group-containing Fc protein and method of producing the same), except that the peptide linker consists of 16 amino acid residues.

The definitions, the examples, and the preferred examples of the Fc protein are the same as those described in the above section of (1. Azide group-containing Fc protein and method of producing the same).

The present invention also provides an azide group-containing Fc protein having an azide group-containing phenylalanine derivative residue at/on the N-terminus of the azide group-containing Fc protein via a peptide linker consisting of 16 amino acid residues, wherein the N terminal amino acid residue of the peptide linker is a lysine residue or an arginine residue.

The present invention also provides a method of producing the azide group-containing Fc protein. The method comprises reacting an azide group-containing phenylalanine derivative with the Fc protein having the above peptide linker at/on the N-terminus by using phenylalanyl tRNA, aminoacyl tRNA synthetase, and leucyl/phenylalanyl tRNA transferase, to yield the azide group-containing Fc protein.

The definitions, the examples, and the preferred examples of the peptide linker for the above azide group-containing Fc protein and method of producing the same are the same as those described in the above section of (1. Azide group-containing Fc protein and method of producing the same), except that the peptide linker consists of 16 amino acid residues.

The definitions, the examples, and the preferred examples of the Fc protein, azide group-containing phenylalanine derivative, and azide group-containing Fc protein for the above azide group-containing Fc protein and method of producing the same are the same as those described in the above section of (1. Azide group-containing Fc protein and method of producing the same).

The definitions, the examples, and the preferred examples of the phenylalanyl tRNA, aminoacyl tRNA synthetase, and leucyl/phenylalanyl tRNA transferase used for the above method of producing an azide group-containing Fc protein are the same as those described in the above section of (1. Azide group-containing Fc protein and method of producing the same). The method of producing an azide group-containing Fc protein can be carried out in the same manner as those described in the above section of (1. Azide group-containing Fc protein and method of producing the same).

Other features of the invention will become apparent in the course of the following descriptions of exemplary embodiments which are given for illustration of the invention and are not intended to be limiting thereof.

EXAMPLES

Example 1: Preparation of Fc Protein Having Cysteine Residue at/on N-Terminus (Cys-Fc)

Figure 2:
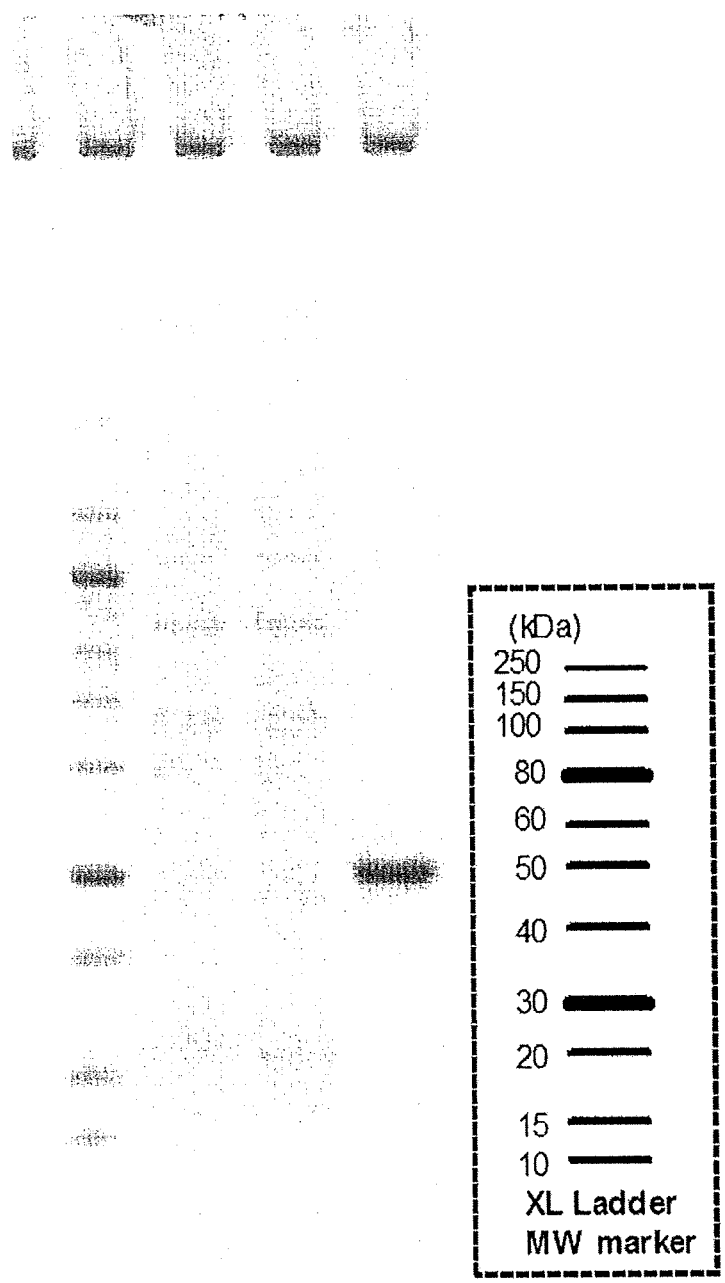
FIG. 2 is a drawing illustrating a result of SDS-PAGE analysis of an effluent after purifying the culture supernatant of Cys-Fc gene-introduced HEK293 cells with protein A. Lane 1: molecular weight marker; lane 2: culture supernatant; lane 3: protein A flow-through; lane 4: protein A effluent.

By using HEK293 cells, the expression of Cys-Fc (human IgG1-derived polypeptide consisting of the amino acid sequence of SEQ ID NO: 1) was carried out. HEK293 cells were transformed with an expression vector obtained by introducing a gene encoding the polypeptide consisting of the amino acid sequence of SEQ ID NO: 2 into pSecTag2/HygroA (Thermo Fisher Scientific) in Opti-MEMI (Thermo Fisher Scientific) medium. The gene encoding the polypeptide consisting of the amino acid sequence of SEQ ID NO: 2 encodes the protein which has a leader sequence [METDTLLLWVLLLWVPGSTG (SEQ ID NO: 3)] added to the N-terminus of the polypeptide consisting of the amino acid sequence of SEQ ID NO: 1. Since the protein secreted from the transformed cells is cleaved at the signal cleavage site adjacently downstream of the leader sequence, Cys-Fc (polypeptide consisting of the amino acid sequence of SEQ ID NO: 1) is secreted into the culture supernatant. The obtained transformed cells were cultured by roller culture (125 rpm) for 5 days under the conditions of 37° C. and 8% $CO_2$ concentration. The culture supernatant was collected by centrifuge and purified by HiTrap Protein A FF (1 mL, GE Healthcare). The effluent was analyzed by SDS-PAGE (Mini-PROTEAN TGX gel, under reducing conditions, Biosafe CBB G-250 staining) and the results are shown in FIG. 2. Furthermore, the obtained Cys-Fc was subjected to an ESI-TOFMS analysis according to the following procedures. The obtained Cys-Fc was subjected to cleavage of glycans by using PNGase F (NEW ENGLAND BioLabs, catalogue No. P0704) according to the manufacturer's protocol. To the solution of Cys-Fc (40 μg), GlycoBuffer 2 (10×, 8 μL) included in the kit was added and water was added to be adjusted to 80 μL. Then, the resultant was added with 4 μL of PNGase F solution 10-fold diluted with water and was mixed followed by incubation for 24 hours at 37° C. The resultant was added with TFA (trifuloroacetic acid) up to the final concentration of 0.2% and was incubated for 30 minutes at 37° C. followed by buffer replacement with 20 mM ammonium acetate (pH 6.5) by using ultrafiltration (Vivaspin 500, 10 k MWCO). To 5 μL of the resulting solution, 2 mM TCEP (tris(2-carboxyethyl)phosphine) aqueous solution (3.5 μL) and water (11.5 μL) were added and mixed. After allowing the resultant to stand for 1 hour at room temperature, an ESI-TOFMS analysis was carried out. The results are shown below.

Molecular weight of Cys-Fc:
Theoretical value: 24836.9
Measured value: 24834.5

Example 2: Preparation of Peptide Linker Thioesters

All of the peptide linker thioesters shown below were prepared by substantially the same method. According to solid phase peptide synthesis using 2-chlorotrityl resin based on Fmoc method, a protected peptide having N-terminal protection with Boc was prepared. Then, the protected peptide was cleaved in 20% HFIP (1,1,1,3,3,3-hexafluoro-2-propanol)/dichloromethane solution. The resultant was concentrated, and dissolved with dichloromethane. After that, HOSu (N-hydroxysuccinimide) (10 molar equivalents), DIPCI (N,N'-diisopropylcarbodiimide) (10 molar equivalents), thiophenol (30 molar equivalents), and DIPEA (N,N-diisopropylethylamine) (10 molar equivalents) were added and stirred 2 overnights at room temperature. The reaction mixture was washed with water and concentrated. The resulting reaction mixture was dissolved in TFA/triisopropylsilane (TIS)/water=95/2.5/2.5 and stirred for 3 hours at room temperature. The reaction mixture was concentrated, and then added and mixed with dichloromethane and water. The aqueous layer was purified by fractionation by HPLC to obtain a peptide linker thioester.

Peptide Linker Thioesters

```
Linker for Fc(4):
KTHT (SEQ ID NO: 4)-SPh

Linker for Fc(8):
KSSDKTHT (SEQ ID NO: 5)-SPh

Linker for Fc(12):
KVEPKSSDKTHT (SEQ ID NO: 6)-SPh

Linker for Fc(13):
KKVEPKSSDKTHT (SEQ ID NO: 7)-SPh

Linker for Fc(16):
KVDKKVEPKSSDKTHT (SEQ ID NO: 8)-SPh
```

(Ph represents phenyl and SPh represents phenylthio).

Example 3: Preparation of Fc Proteins Having Lysine Residue at/on N-Terminus The Fc proteins were prepared according to the Patent Literature (U.S. Pat. No. 7,404,956), and the Non Patent Literature (Proc. Jap. Acad. Ser. B, 2011, 603). Into 50 mM MES buffer (pH 6.5) containing 1.0 mM TCEP-HCl and 10 mM MPAA (4-mercaptophenylacetic acid), 0.02 mM Cys-Fc (prepared in Example 1) and 0.4 mM peptide linker thioester (prepared in Example 2) were dissolved and stirred overnight at 25° C. The reaction solution was replaced with 20 mM acetic acid buffer (pH 5.5) using Vivaspin 500 (10 k MWCO, Sartorius), and then purified by Resource S (1 mL, GE Healthcare).

The Fc proteins having a lysine residue at/on the N-terminus obtained in Example 3 are as follows.

```
Fc(4):
KTHT (SEQ ID NO: 4)-Fc protein (SEQ ID NO: 1)

Fc(8):
KSSDKTHT (SEQ ID NO: 5)-Fc protein (SEQ ID NO: 1)

Fc(12):
KVEPKSSDKTHT (SEQ ID NO: 6)-Fc protein
(SEQ ID NO: 1)

Fc(13):
KKVEPKSSDKTHT (SEQ ID NO: 7)-Fc protein
(SEQ ID NO: 1)

Fc(16):
KVDKKVEPKSSDKTHT (SEQ ID NO: 8)-Fc protein
(SEQ ID NO: 1)
```

(Peptide linker and Fc protein bind to each other via an amide bond, because the peptide linker thioester reacts with the amino group of the N terminal cysteine residue of an Fc protein to yield an amide bond).

Example 4: Preparations of Enzymes and tRNA

Two kinds of enzymes and a tRNA, which are used for the reaction between an Fc protein having a lysine residue at/on the N-terminus and a phenylalanine derivative, were prepared. Specifically, the leucyl/phenylalanyl-tRNA-protein transferase (L/F-Transferase) was prepared according to the method described in ChemBioChem 2006, 1676; and J. Biol. Chem. 1995, 20631, both of which are incorporated herein by reference in their entireties. Double-mutated ARS was prepared according to ChemBioChem 2009, 2460; J. Am. Chem. Soc. 2002, 5652; and ChemBioChem 1991, 99, all of which are incorporated herein by reference in their entireties. $tRNA^{Phe}$ was prepared according to ChemBioChem 2009, 2460; and Nucleic Acids Res 1996, 907, both of which are incorporated herein by reference in their entireties.

Example 5: Difference in Reactivity Caused by N Terminal Sequence of Fc Protein (5-1) Preparation of Substance of Interest that is Added with Ring Having Triple Bond Between Carbon Atoms By using PEG as a substance of interest, a substance of interest added with a ring having a triple bond between carbon atoms (PEG-DIBAC) was prepared according to the following procedures. 16.1 mg of DIBAC acid (5-(5,6-dihydro-11,12-didehydrodibenzo[b,f]azocin-5(6H)-yl)-5-oxopentanoic acid) were dissolved in 1 mL of dichloromethane, added with 14.7 mg of EDC-HCl, 11.7 mg of HOBt-$H_2O$, and 17.5 μL of diisopropylethylamine, added with 102.2 mg of methoxypolyethylene glycol propylamine (SUNBRIGHT MEPA-20H), and then mixed overnight at room temperature. The reaction mixture was washed with a saturated aqueous solution of ammonium chloride and saturated brine. After that, the solvent was distilled off and purification was carried out by silica gel column chromatography to obtain 94 mg of PEG-DIBAC.

(5-2) Preparation of Azide Group-Containing Fc Protein

To a reaction vessel, 4 μL of solution A (500 mM HEPES, pH 7.6, 100 mM $MgCl_2$, 10 mM spermidine) and 4 μL of solution B (25 mM ATP and 200 mM KCl) were added, and then 2 μL of $tRNA^{Phe}$ aqueous solution (0.10 O.D./μL), 4.5 μL of a double-mutant aminoacyl-tRNA synthetase solution (17.8 μM), 2.1 μL of L/F-transferase (39 μM), 14.5 μL of 4-azidophenylalanine (1 mM), and 3.4 μL of water were added and admixed with one another. To the resultant, a solution of the Fc protein having peptide linker with various chain length (1.2 to 2.3 mg/mL), as it was obtained in Example 3, was added in an amount of 5.5 μL and shaken for 5 hours at 37° C. Thereby, an azide group-containing Fc protein resulting from a reaction of 4-azidophenylalanine and the above Fc protein was obtained.

(5-3) Preparation of Fc Protein Derivative Added with Substance of Interest

To the reaction solution obtained in (5-2), 30 μL of a DMSO solution (2 mM) of PEG-DIBAC obtained in (5-1) were added and shaken overnight at 25° C. Thereby, a reaction between the azide group-containing Fc protein and PEG-DIBAC occurred to yield a PEGylated Fc protein (the two types of addition modes of azide group to DIBAC represented by the following formula are considered).

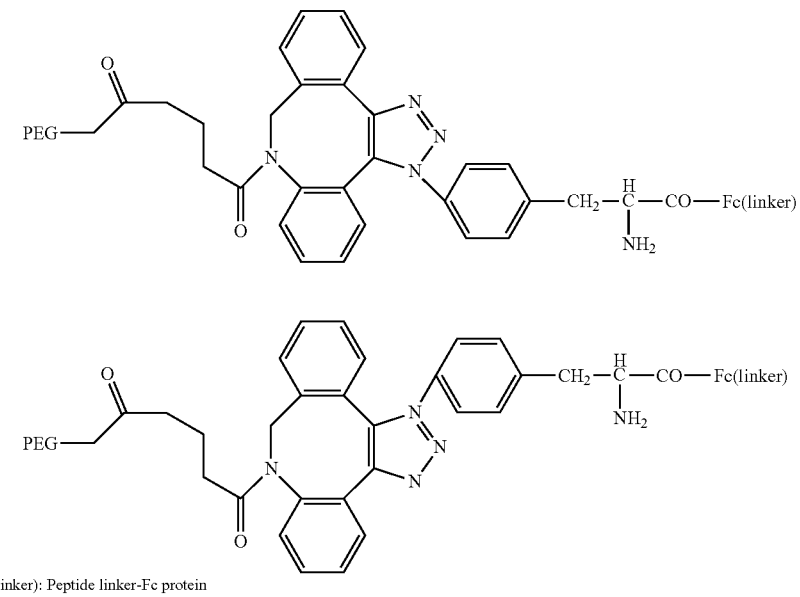

Fc(linker): Peptide linker-Fc protein

Figure 3:
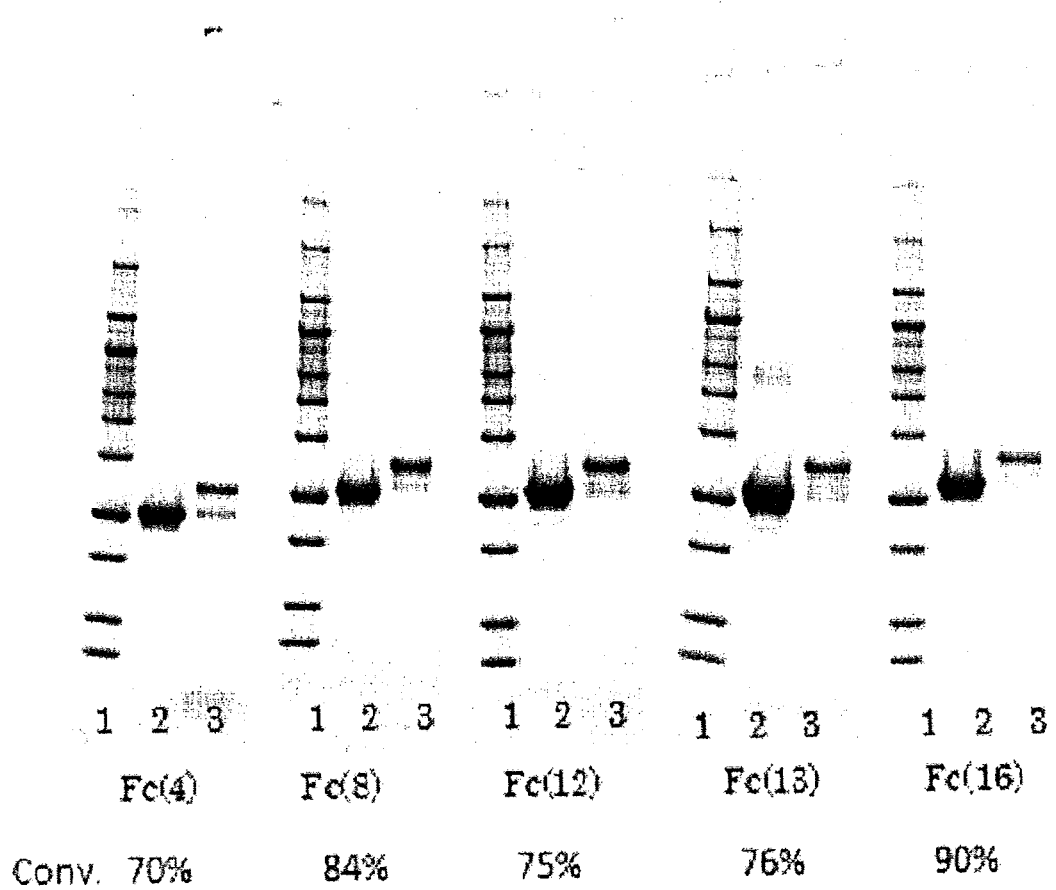
FIG. 3 is a drawing illustrating an SDS-PAGE evaluation of the rate of conversion into an azide group-containing Fc protein in the synthesis of an azide group-containing Fc protein (see, Reaction A of FIG. 1). The synthesis of the azide group-containing Fc protein was carried out according to the addition of an azide group-containing phenylalanine derivative (4-azidophenylalanine) to the following various Fc proteins by using phenylalanyl tRNA (tRNA$^{Phe}$), aminoacyl tRNA synthetase (double-mutant aminoacyl-tRNA synthetase), and leucyl/phenylalanyl tRNA transferase (L/F-transferase). Conv.: rate of conversion. Fc(4): KTHT (SEQ ID NO: 4)-Fc protein (rate of conversion: 70%); Fc(8): KSSDKTHT (SEQ ID NO: 5)-Fc protein (rate of conversion: 84%); Fc(12): KVEPKSSDKTHT (SEQ ID NO: 6)-Fc protein (rate of conversion: 75%); Fc(13): KKVE-PKSSDKTHT (SEQ ID NO: 7)-Fc protein (rate of conversion: 76%); Fc(16): KVDKKVEPKSSDKTHT (SEQ ID NO: 8)-Fc protein (rate of conversion: 90%). Lane 1: molecular weight marker (the same as in FIG. 2); lane 2: various Fc proteins before the reaction (negative control); lane 3: reaction mixture in the synthesis of the azide group-containing Fc protein (upper band: a PEGylated protein; lower band: a non-PEGylated protein).

The obtained reaction mixture was purified by Protein A (Aspire Protein A Tips, Thermo), and the result obtained by analyzing the effluent by SDS-PAGE (Mini-PROTEAN TGX gel, 4 to 20%, BIO-RAD) is illustrated in FIG. 3.

As a result, it was recognized that all the Fc proteins in which the peptide linker at/on the N-terminus has length of 4 to 16 amino acid residues have high conversion rate of 70% or higher for both the reaction with phenylalanine derivative (4-azidophenylalanine) and the reaction with PEG-DIBAC thereafter, while the conversion rate varies depending on the length of a peptide linker (FIG. 3). The Fc(16) in which the peptide linker at/on the N-terminus has length of 16 amino acid residues showed extremely high conversion rate, that is, 90% (FIG. 3).

Comparative Example 1: Method of Producing Fc Protein Derivative Added with Substance of Interest Based on S-Alkylation Reaction As a substance of interest, a peptide consisting of the amino acid sequence of SEQ ID NO: 9 (Exenatide-Cys: peptide having cysteine added to the C-terminus of the peptide pharmaceutical named Exenatide) was prepared by a solid phase peptide synthesis.

To a reaction vessel, 8 μL of solution A (500 mM HEPES, pH 7.6, 100 mM MgCl$_2$, 10 mM spermidine) and 8 μL of solution B (25 mM ATP and 200 mM KCl) were added, and then 4 μL of tRNA$^{Phe}$ aqueous solution (0.10 O.D./μL), 9 μL of a double-mutant aminoacyl-tRNA synthetase solution (17.8 μM), 4.1 μL of L/F-transferase (39 μM), 29 μL of 4-(chloroacetamide)phenylalanine (11 mM), and 9.5 μL of water were added and admixed with one another. To the resultant, 8.3 μL of an Fc(16) solution (2.5 mg/mL) were added and shaken for 5 hours at 37° C. Thereby, an chloroacetamide group-containing Fc protein resulting from a reaction of 4-(chloroacetamide)phenylalanine and Fc(16) was obtained.

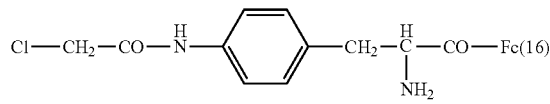

Fc(16): Peptide linker (16aa)-Fc protein
(SEQ ID NO: 8)

The obtained reaction mixture was purified by Protein A (Aspire Protein A Tips, Thermo), and the effluent was replaced with 0.1 M HEPES buffer, pH 7.5 and then concentrated to 25 μL by ultrafiltration. To the resultant, 5 μL of an aqueous solution (18 mM) of the peptide (SEQ ID NO: 9) (100 equivalents of peptide (SEQ ID NO: 9) are contained relative to the amount of the chloroacetamide group-containing Fc protein) were added and mixed followed by shaking for 4 days at 25° C. Thereby, an Fc protein derivative added with the peptide (SEQ ID NO: 9), which results from a reaction of chloroacetamide group-containing Fc protein and the peptide (SEQ ID NO: 9), was obtained.

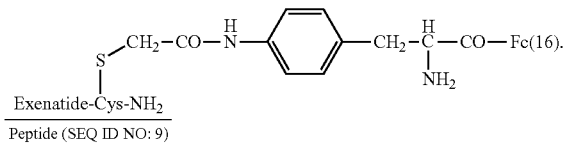

Peptide (SEQ ID NO: 9)

Figure 4:
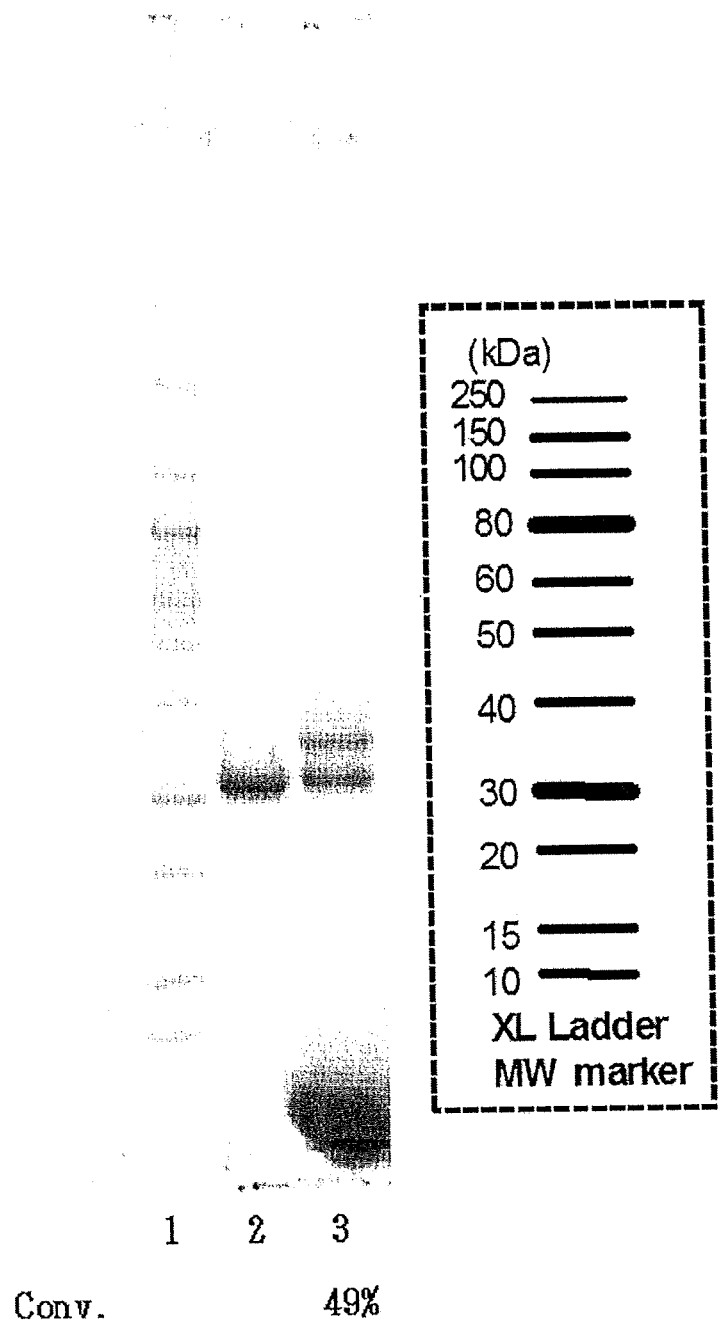
FIG. 4 is a drawing illustrating an SDS-PAGE evaluation of the rate of conversion into an Fc protein derivative in the synthesis of an Fc protein derivative added with a substance of interest (Comparative Example of Reaction B in FIG. 1). The synthesis of the Fc protein derivative added with the substance of interest (Comparative Example) was carried out according to a reaction between the Fc protein and the substance of interest based on S-alkylation reaction. Conv.: rate of conversion. Lane 1: molecular weight marker; lane 2: Fc protein Fc(16) before the reaction (negative control); lane 3: reaction mixture for synthesis of the Fc protein derivative added with the peptide of interest (rate of conversion: 49%).

The result obtained by analyzing the obtained reaction mixture by SDS-PAGE (Mini-PROTEAN TGX gel, 4 to 20%, BIO-RAD; under reducing conditions; stained by SYPRO (registered trademark) Ruby) is illustrated in FIG. 4.

As a result, the reaction efficiency of the Fc protein for S-alkylation reaction was 49% when the peptide was used in an amount of about 100 equivalents relative to the amount of the Fc protein (FIG. 4).

Example 6: Method of Producing Fc Protein Derivative Added with Substance of Interest Based on SPAAC Reaction (6-1) Preparation of Azide Group-Containing Fc Protein To a reaction vessel, 16 μL of solution A (500 mM HEPES, pH 7.6, 100 mM MgCl$_2$, 10 mM spermidine) and 16 μL of solution B (25 mM ATP and 200 mM KCl) were added, and then 8 μL of tRNA$^{Phe}$ aqueous solution (0.10 O.D./μL), 18 μL of a double-mutant aminoacyl-tRNA synthetase solution (17.8 μM), 8.2 μL of L/F-transferase (39 μM), 58.2 μL of 4-azidophenylalanine (11 mM), and 19 μL of water were added and admixed with one another. To the resultant, 16.6 μL of an Fc(16) solution (2.5 mg/mL) were added and shaken for 6 hours at 37° C. Thereby, an azide group-containing Fc protein represented by the following formula, which results from a reaction of 4-azidophenylalanine and Fc(16), was obtained.

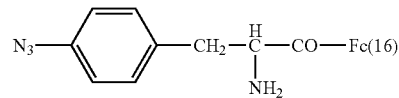

Fc(16): Peptide linker (16aa)-Fc protein
(SEQ ID NO: 8)

The obtained reaction mixture was purified by Protein A (Aspire Protein A Tips, Thermo), and the effluent was replaced with 0.1 M sodium phosphate buffer (pH 7.0), and then concentrated to 65 μL by ultrafiltration. As a result of quantifying the azide group-containing Fc protein based on A280 method, the result was found to be 0.49 mg/mL.

Furthermore, Fc(16) used herein and the azide group-containing Fc protein prepared herein were analyzed by ESI-TOFMS according to the following procedures. By using PNGase F (NEW ENGLAND BioLabs, catalogue No. P0704), each of Fc(16) and azide group-containing Fc protein was subjected to cleavage of glycans according to the manufacturer's protocol. To a solution of each compound (40 μg), GlycoBuffer 2 (10×, 8 μL) included in the kit was added and the resultant was adjusted to 80 μL by adding water. Then, 4 μL of PNGase F solution, which was diluted 10-folds with water, were added thereto, and after mixing, incubated for 24 hours at 37° C. TFA was then added up to the final concentration of 0.2%. After incubation for 30 minutes at 37° C., the resultant was replaced with 20 mM ammonium acetate (pH 6.5) buffer by using ultrafiltration (Vivaspin 500, 10 k MWCO). To 5 μL of the obtained solution, 2 mM TCEP aqueous solution (3.5 μL) and water (11.5 μL) were added and mixed. After allowing it to stand for 1 hour at room temperature, an ESI-TOFMS analysis was carried out therefor. The results are shown below.

Molecular weight of Fc(16):
Theoretical value: 26645.9
Measured value: 26643.8
Molecular weight of azide group-containing Fc protein:
Theoretical value: 26834.1
(Theoretical value of azide group reduced form: 26808.1)
Measured value: 26805.7

(6-2) Preparation of Substance of Interest Added with Ring Having Triple Bond Between Carbon Atoms By having a peptide consisting of the amino acid sequence of SEQ ID NO: 9 as a substance of interest, a substance of interest added with a ring having a triple bond between carbon atoms (peptide-DBCO adduct) was prepared according to the following procedures. To 7.6 mg of the peptide consisting of the amino acid sequence of SEQ ID NO: 9, 818 μL of 0.1 M sodium phosphate buffer (pH 7.0) were added and then 88 μL of DBCO (dibenzocyclooctyne)-maleimide (Tokyo Chemical Industries, 40 mM in DMSO) were added thereto and mixed therein followed by shaking for 4 hours at 25° C. The resultant was repeatedly subjected to, 4 times in total, concentration by ultrafiltration (Amicon Ultra-4, 3 k MWCO) and dilution with water. The obtained aqueous solution was subjected to freeze-drying to obtain 7.1 mg of peptide-DBCO adduct. ESI-MS (positive mode) m/z; 1572.5, 1179.9, 944.0, 786.9

(6-3) Preparation of Fc Protein Derivative Added with Substance of Interest

To 4 μL of a solution of the azide group-containing Fc protein obtained in (6-1), 7.6 μL of 0.1 M sodium phosphate buffer (pH 7.0) and 1.5 μL of a solution of 0.10 mM peptide (SEQ ID NO: 9)-DBCO adduct obtained in (6-2) were added (containing 2 equivalents of peptide (SEQ ID NO: 9)-DBCO adduct relative to the amount of azide group-containing Fc protein), and shaken overnight at 25° C. Thereby, an Fc protein derivative added with a peptide (SEQ ID NO: 9) resulting from a reaction of an azide group-containing Fc protein and peptide (SEQ ID NO: 9)-DBCO adduct was obtained (following two types represented by the formula shown below are considered as an addition mode of azide group to DBCO).

80 μL by adding water. Then, the resultant was added with 4 μL of PNGase F solution, which was diluted 10-folds with water, and, after mixing, incubated for 24 hours at 37° C. The resultant was added with TFA (trifuloroacetic acid) to have final concentration of 0.2% followed by incubation for 30 minutes at 37° C. The resultant was then subjected to buffer replacement with 20 mM ammonium acetate (pH 6.5) by using ultrafiltration (Vivaspin 500, 10 k MWCO). To 5 μL of the resulting solution, 2 mM TCEP aqueous solution (3.5 μL) and water (11.5 μL) were added and mixed. After allowing the resultant to stand for 1 hour at room temperature, an ESI-TOFMS analysis was carried out therefor. The results are shown below.

Molecular weight of the Fc protein derivative added with a peptide (SEQ ID NO: 9):

Theoretical value: 31551.3

(Theoretical value of hydrolyzate: 31569.3)

Measured value: 31567.3

Figure 5:
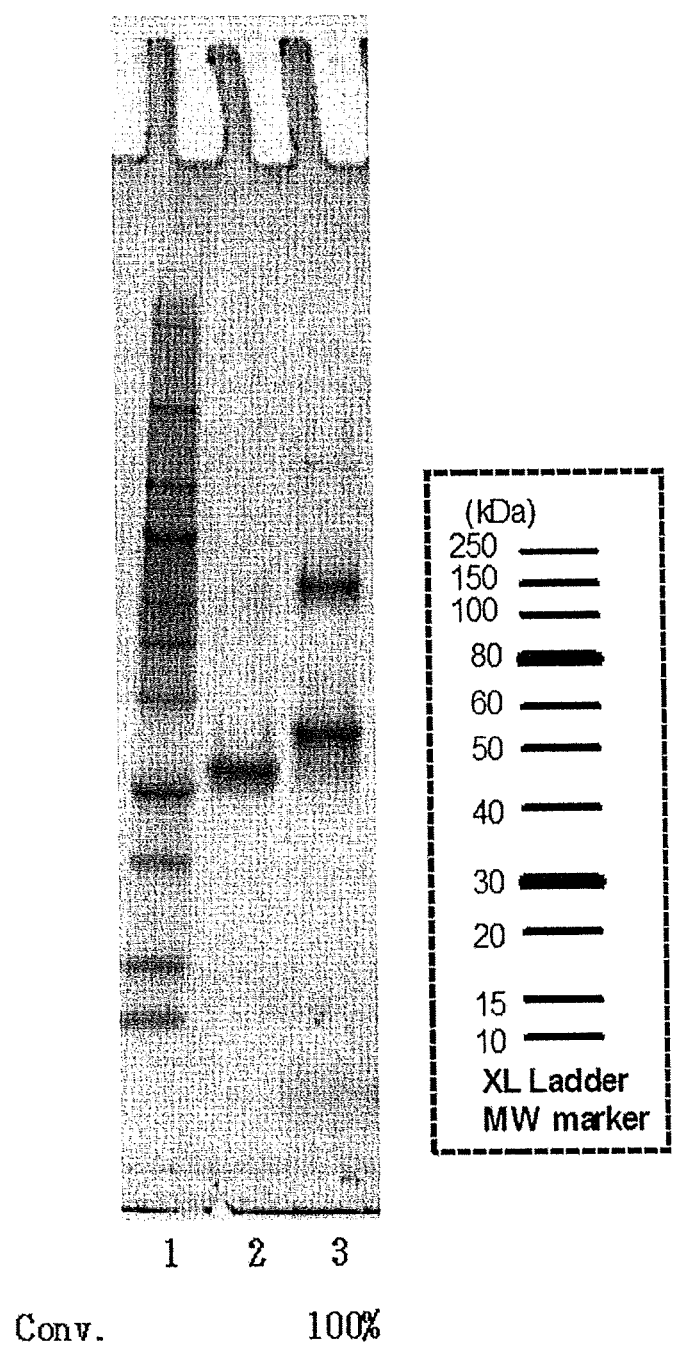
FIG. 5 is a drawing illustrating an SDS-PAGE evaluation of the rate of conversion into an Fc protein derivative in the synthesis of an Fc protein derivative added with a substance of interest (Reaction B in FIG. 1). The synthesis of the Fc protein derivative added with the substance of interest was carried out according to a reaction between the azide group-containing Fc protein and the substance of interest based on SPAAC reaction. Conv.: rate of conversion. Lane 1: molecular weight marker; lane 2: Fc protein Fc(16) before the reaction (negative control); lane 3: reaction mixture for synthesis of the Fc protein derivative added with the peptide of interest (rate of conversion: 100%).

As a result, it was shown that the reaction efficiency of the azide group-containing Fc protein by SPAAC reaction exhibited a extremely high value, that is, 100%, even when the peptide was used in a small amount like 2 equivalents relative to the amount of the azide group-containing Fc protein (FIG. 5).

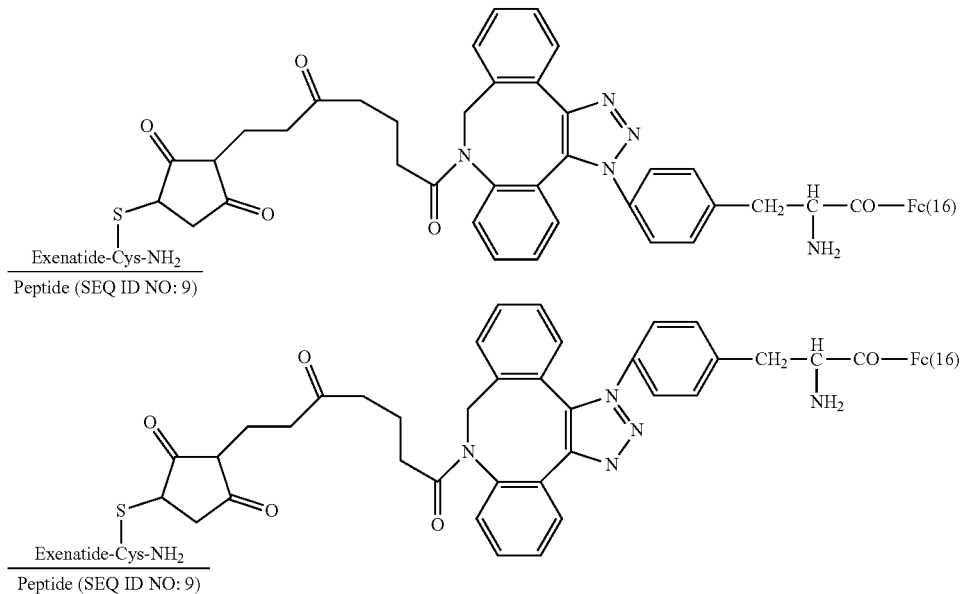

The result obtained by analyzing the obtained reaction mixture by SDS-PAGE (Mini-PROTEAN TGX gel, 4 to 20%, BIO-RAD; under reducing conditions; stained by SYPRO (registered trademark) Ruby) is illustrated in FIG. 5. Furthermore, the obtained Fc protein derivative added with a peptide (SEQ ID NO: 9) was subjected to an ESI-TOFMS analysis according to the following procedures. By using PNGase F (NEW ENGLAND BioLabs, catalogue No. P0704), the obtained Fc protein derivative added with a peptide (SEQ ID NO: 9) was subjected to cleavage of glycans according to the manufacturer's protocol. To a solution of the obtained Fc protein derivative added with a peptide (SEQ ID NO: 9) (40 μg), GlycoBuffer 2 (10×, 8 μL) included in the kit was added and it was adjusted to Example 7: Preparation of Fc Protein Having Lysine Residue at/on N-Terminus (Lys-Fc) by Using Cultured Cells (7-1) Construction of YDK0107 Strain By using secretory expression plasmid pPKK50TEV-Teri of Teriparatide, which is a physiologically active peptide, described in WO 2014/126260 A, C. glutamicum YDK010 strain described in WO 2002/081694 A was transformed. Furthermore, pPKK50TEV-Teri is a vector for secretory expression of Teriparatide as a physiologically active peptide, and it is a plasmid having a nucleotide sequence encoding the promoter region of cspB gene of C. glutamicum ATCC13869 strain, CspB signal peptide of the same strain which is linked, in a mode of enabling the expression, to the downstream of the same promoter, 50 amino acid residues at/on the N-terminus of mature CspB of the same strain, sequence ENLYFQ (SEQ ID NO: 10) recognizing ProTEV protease, and fusion protein of Teriparatide (hereinbelow, described as CspB50TEV-Teri) (WO 2014/126260 A, which is incorporated herein by reference in its entirety). *C. glutamicum* YDK010 strain is *C. glutamicum* AJ12036 (FER M BP-734) strain deficient of cell surface layer protein CspB (WO 2002/081694 A). The obtained transformants were cultured at 30° C. on CMDex agar medium containing 25 mg/L kanamycin (glucose 5 g, magnesium sulfate heptahydrate 0.4 g, iron sulfate heptahydrate 0.01 g, manganese sulfate pentahydrate 0.01 g, potassium dihydrogen phosphate 1 g, biotin 10 μg, Difco™ Select Soytone (Becton Dickinson) 10 g, Bacto™ Yeast Extract (Becton Dickinson) 10 g, urea 3 g, HCl-hydrolyzed solution of soybean (total nitrogen amount: 1.2 g), agar powder 20 g, adjusted to pH 6.5 after having 1 L with water) to form a colony.

After culturing, a natural mutant strain introduced with a mutation in phoS gene was selected and named YDK0107 strain.

(7-2) Construction of pPK6 Vector (a) Construction of Vector (pPK5) with Modified NaeI Recognition Site in pPK4 Vector In pPK4 described in JP 9-322774 A, there is one recognition site for the restriction enzyme NaeI. To modify this sequence, the primers described in SEQ ID NO: 11 and SEQ ID NO: 12 comprising a modified sequence, in which gccggc as the recognizing sequence of NaeI is modified to gcaggc, and a neighboring sequence thereof in pPK4 were synthesized. Next, by having pPK4 as a template and using the primers described in SEQ ID NO: 11 and SEQ ID NO: 12, the whole-length plasmid of about 5.6 kbp was amplified by PCR. For the PCR, Pyrobest (registered trademark) DNA polymerase (Takara Bio) was used and the PCR was carried out at the following reaction conditions; 95° C. for 5 minutes, (95° C. for 30 seconds, 55° C. for 1 minute, 72° C. for 12 minutes)×12 cycles.

Next, the obtained PCR product was treated with the restriction enzyme DpnI and the methylated template DNA was digested. The non-methylated plasmid obtained after DpnI digestion was introduced to competent cells of *E. coli* JM109 (Takara Bio) to obtain the plasmid. As a result of nucleotide sequencing, it was confirmed as expected that a plasmid with modified NaeI recognition site is constructed. The nucleotide sequencing was carried out by using BigDye (registered trademark) Terminator v3.1 Cycle Sequencing Kit (Applied Biosystems) and 3130 Genetic Analyzer (Applied Biosystems). The vector having modified NaeI recognition site in pPK4 vector, which was obtained as above, was named pPK5.

(b) Construction of Vector Carrying tatABC Gene in pPK5 Vector (pPK5-tatABC)

Next, by using pVtatABC, which is an amplification plasmid of Tat-system secretion machinery described in WO 2005/103278 A, as a template and also primers described in SEQ ID NO: 13 and SEQ ID NO: 14, the DNA fragment of about 3.7 kbp comprising the sequence encoding tatABC gene was amplified by PCR. In the primer described in SEQ ID NO: 14, recognition sequences for the restriction enzymes KpnI and ApaI are designed. For the PCR, Pyrobest (registered trademark) DNA polymerase (Takara Bio) was used, and the reaction conditions were the same as the protocol recommended by the manufacturer. Terminal of the DNA fragment was phosphorylated by using BKL Kit (Takara Bio) followed by separate treatment with KpnI. Furthermore, a blunt-end treatment was carried out by using BKL Kit (TakaraBio), and the terminal was inserted to the dephosphoylated pPK5 vector by using CIAP (Takara Bio) to construct pPK5-tatABC which is a vector carrying tatABC gene. For the ligation, DNA Ligation Kit Ver. 2.1 (Takara Bio) was used, and the reaction conditions were the same as the protocol recommended by the manufacturer. As a result of nucleotide sequencing of the inserted fragment, it was confirmed that the gene was inserted as expected. The nucleotide sequencing was carried out by using BigDye (registered trademark) Terminator v3.1 Cycle Sequencing Kit (Applied Biosystems) and 3130 Genetic Analyzer (Applied Biosystems).

(c) Construction of vector (pPK6) with modified KpnI and XbaI recognition sites within tatABC gene in pPK5-tatABC vector Within the tatABC gene region in the pPK5-tatABC plasmid constructed in the preceding item, recognition sites for the restriction enzymes KpnI and XbaI are present, one for each enzyme. To modify their sequences, the primers described in SEQ ID NO: 15 and SEQ ID NO: 16 comprising a sequence, in which ggtacc as a recognizing sequence of KpnI is modified to ggaacc, and a neighboring sequence in pPK5-tatABC, and the primers described in SEQ ID NO: 17 and SEQ ID NO: 18 comprising a sequence, in which tctaga as a recognizing sequence of XbaI is modified to tgtaga, and a neighboring sequence in pPK5-tatABC were synthesized.

First, by having pPK5-tatABC as a template and using the primers described in SEQ ID NO: 15 and SEQ ID NO: 16, the whole-length plasmid of about 9.4 kbp was amplified by PCR such that KpnI recognition site within tatABC gene region is modified. For the PCR, Pyrobest (registered trademark) DNA polymerase (Takara Bio) was used and the PCR was carried out at the following reaction conditions; 95° C. for 5 minutes, (95° C. for 30 seconds, 55° C. for 1 minute, 72° C. for 12 minutes)×12 cycles.

Next, the obtained PCR product was treated with the restriction enzyme DpnI and the methylated template DNA was digested. The non-methylated plasmid obtained after DpnI digestion was introduced to competent cells of *E. coli* JM109 (Takara Bio) to obtain the plasmid. Thereby, construction of pPK5-tatABCΔKpnI, which is a vector having modified KpnI recognition site within tatABC gene region, was achieved.

Next, by having pPK5-tatABCΔKpnI as a template and using primers described in SEQ ID NO: 17 and SEQ ID NO: 18, the whole-length plasmid of about 9.4 kbp was amplified by PCR such that XbaI recognition site within tatABC gene region is modified. For the PCR, Pyrobest (registered trademark) DNA polymerase (Takara Bio) was used and the PCR was carried out at the following reaction conditions; 95° C. for 5 minutes, (95° C. for 30 seconds, 55° C. for 1 minute, 72° C. for 12 minutes)×12 cycles.

Next, the obtained PCR product was treated with the restriction enzyme DpnI and the methylated template DNA was digested. The non-methylated plasmid obtained after DpnI digestion was introduced to competent cells of *E. coli* JM109 (Takara Bio) to obtain the plasmid. Thereby, pPK5-tatABCΔKpnIΔXbaI was obtained as a vector having modified XbaI recognition site within tatABC gene region. As a result of nucleotide sequencing, it was confirmed that the gene construction is achieved as expected. The nucleotide sequencing was carried out by using BigDye (registered trademark) Terminator v3.1 Cycle Sequencing Kit (Applied Biosystems) and 3130 Genetic Analyzer (Applied Biosystems).

Thus-obtained vector carrying tatABC gene based on pPK4 vector was named pPK6.

(7-3) Preparation of Fc Protein Having Lysine Residue at/on N-Terminus (Lys-Fc)

An expression vector having Lys-Fc gene (SEQ ID NO: 19 and SEQ ID NO: 20) introduced to pPK6 described in (7-2) was prepared, and, by using it, transformation of the *Corynebacterium glutamicum* YDK0107 strain obtained in (7-1) was carried out. Each of the obtained transformants was cultured at 30° C. for 72 hours on MMTG liquid medium containing 25 mg/L kanamycin (glucose 120 g, magnesium sulfate heptahydrate 3 g, ammonium sulfate 30 g, potassium dihydrogen phosphate 1.5 g, iron sulfate heptahydrate 0.03 g, manganese sulfate pentahydrate 0.03 g, thiamine hydrochloride 0.45 mg, biotin 0.45 mg, DL-methionine 0.15 g, HCl-hydrolyzed solution of soybean (total nitrogen amount: 0.2 g), calcium carbonate 50 g, adjusted to pH 7.0 after having 1 L with water). Upon the completion of the culture, each culture was centrifuged to obtain the culture supernatant.

The culture supernatant containing the Fc protein (less than 9 mL) was filtered through a MILLEX-GV filter (0.22 μm, φ13 mm) and the resultant was concentrated by centrifuge using an ultrafiltration membrane (Amicon Ultra-4, 10 k MWCO) and subjected to buffer replacement using added PBS solution. By using 100 μL of the 160 μL concentrate, refolding was carried out. To the concentrate, 8 M guanidine-HCl in 20 mM sodium phosphate, pH 8.0 (300 μL) was added followed mixing and stirring for 1.5 hours at 37° C. To the resultant, 200 mM DTT in 100 mM Tris-HCl, pH 8.4 (6 μL) was added followed by mixing and further stirring for 1.5 hours at 37° C. The mixture liquid was cooled to 5° C., and the whole amount of the cooled refolding premix (Table 1) was added and mixed, and then allowed to stand overnight in a refrigerator. The refolding solution was dialyzed against PBS using a dialysis membrane (SpectroPor, Float-A-Lyzer G2 5 mL, 3.5 to 5 k MWCO) and further concentrated using an ultrafiltration membrane (Amicon Ultra-4, 10 k MWCO) to obtain the refolding mixture in an amount of 300 μL.

Figure 6:
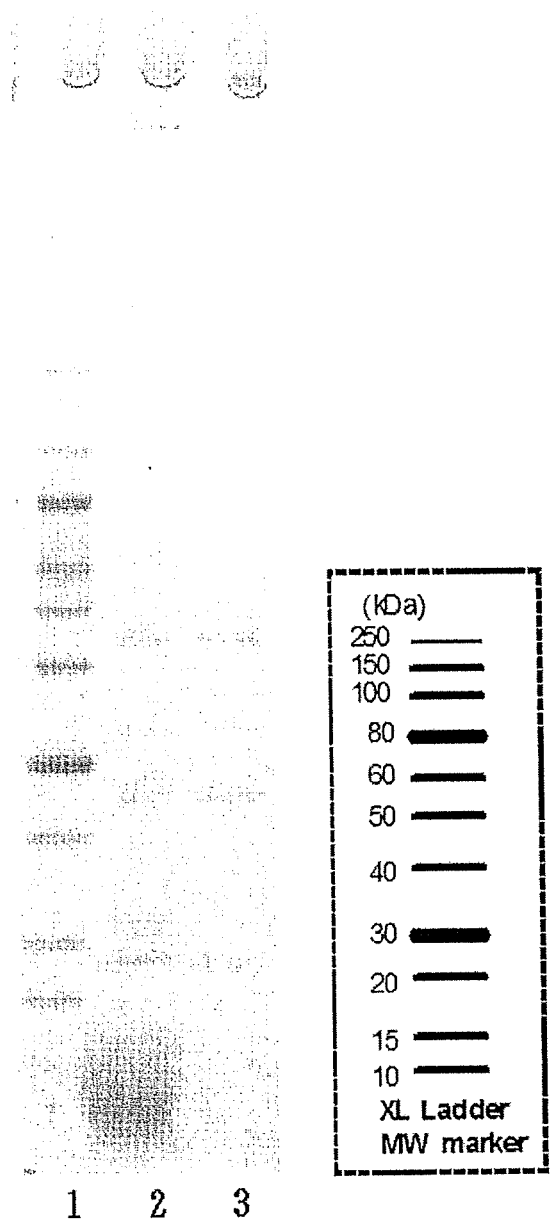
FIG. 6 is a drawing illustrating a result of SDS-PAGE analysis of the Fc protein having a lysine residue at/on the N-terminus (Lys-Fc) produced by using transformed cells, in which the analysis was made based on. Lane 1: molecular weight marker; lane 2: Refolding Mixture; lane 3: Fc protein having a lysine residue at/on the N-terminus (the Fc protein produced in Example 7).

The obtained product was purified by Protein A (Aspire Protein A Tips, Thermo) and the effluent was concentrated using an ultrafiltration membrane (Vivaspin 500, 10 k MWCO) and then subjected to PBS replacement to obtain an Fc protein having a lysine residue at/on the N-terminus (Lys-Fc) in an amount of 100 μL. As a result of quantification based on A280 method, the Fc protein was calculated to be 0.69 mg/mL in the obtained solution. Result of the SDS-PAGE (Mini-PROTEAN TGX gel; under non-reducing conditions; Bio-safe CBB G-250 staining) is illustrated in FIG. 6.

TABLE 1

| Composition of refolding premix | |
|---|---|
| | Volume |
| 2M Arginine-HCl in 20 mM Tris-HCl, pH 8.0 | 2000 μL |
| Water | 1396 μL |
| 1M Tris-HCl, pH 8.0 | 155.2 μL |
| 0.5M Glutathione (reduced form), 20 mM Tris-HCl | 8 μL |
| 0.1M Glutathione (oxidized form), 20 mM Tris-HCl | 40 μL |

Based on the above, it was confirmed that an Fc protein having a lysine residue at/on the N-terminus can be produced by using cultured cells.

Example 8: Method of Producing Fc Protein Derivative Added with Non-Natural Cyclic Peptide Based on SPAAC Reaction (8-1) Preparation of Substance of Interest Added with Ring Having Triple Bond Between Carbon Atoms (Non-Natural Cyclic Peptide-DBCO Adduct)

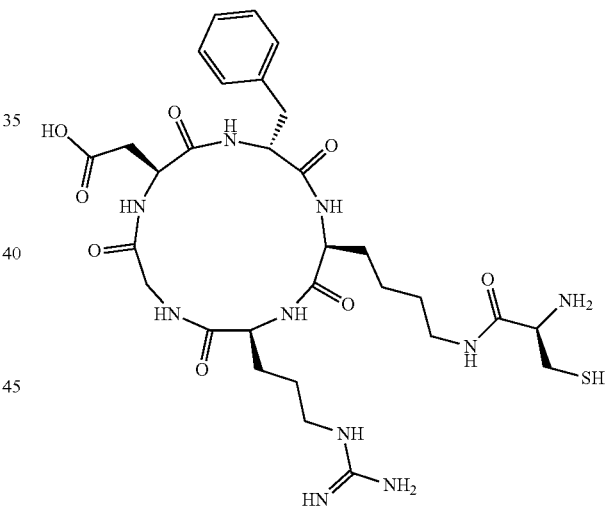

As a substance of interest, 18.3 mg of a non-natural cyclic peptide of the above formula were dissolved in 913 μL of water, and to 663 μL of the resulting solution, 70.4 μL of DBCO (dibenzocyclooctyne)-maleimide (Tokyo Chemical Industries, 40 mM in DMSO) and 150.6 μL of DMSO were added and admixed with one another followed by shaking for 20 hours at room temperature. The reaction mixture was purified by fractional HPLC (Inertsil ODS-3, φ20×250 mm, eluent A; 100 mM ammonium acetate aqueous solution, eluent B; acetonitrile, linear gradient of from 33% B to 53% B). The obtained fraction was freeze-dried to obtain 9.8 mg of a non-natural cyclic peptide-DBCO adduct of the following formula. ESI-TOFMS (positive mode) m/z; 1134.5

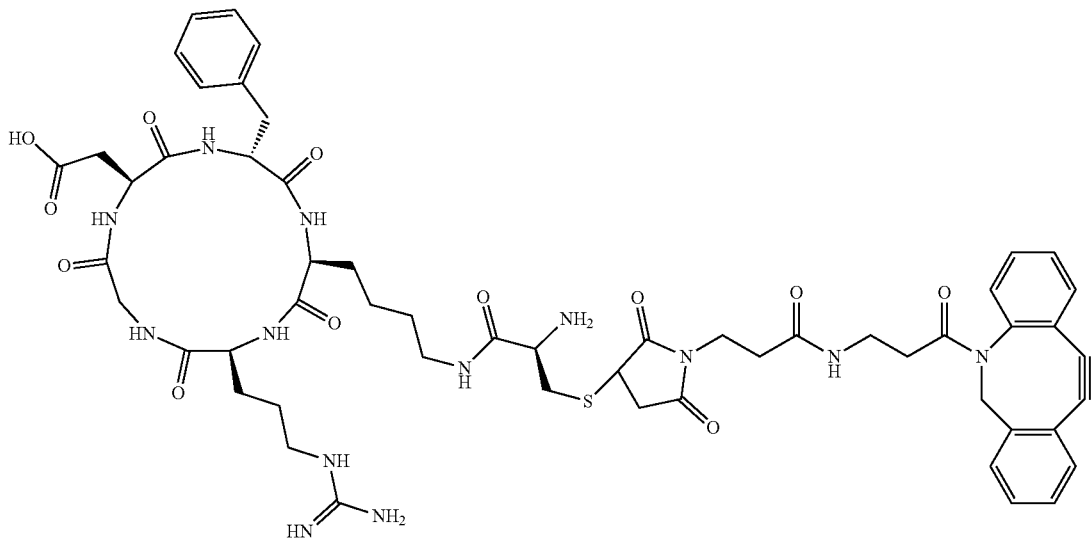 [SMILES: N=C(N)NCCC[C@@H]1NC(=O)[C@H](CCCCNC(=O)[C@@H](N)CSC2CC(=O)N(CCC(=O)NCCC(=O)N3Cc4ccccc4C#Cc4ccccc43)C2=O)NC(=O)[C@@H](Cc2ccccc2)NC(=O)[C@H](CC(=O)O)NC(=O)CNC1=O]

(8-2) Preparation of Fc Protein Derivative Added with Substance of Interest

To 6.6 μL of a solution of the azide group-containing Fc protein (containing 50 μg of azide group-containing Fc protein), 24.4 μL of 0.1 M sodium phosphate buffer (pH 7.0) and 7.4 μL of a 2.5 mM aqueous solution of non-natural cyclic peptide-DBCO adduct obtained in (8-1) were added, and shaken overnight at 25° C. Thereby, an Fc protein derivative added with a non-natural cyclic peptide resulting from a reaction of an azide group-containing Fc protein and a non-natural cyclic peptide-DBCO adduct was obtained (following two types represented by the formula shown below are considered as an addition mode of azide group to DBCO).

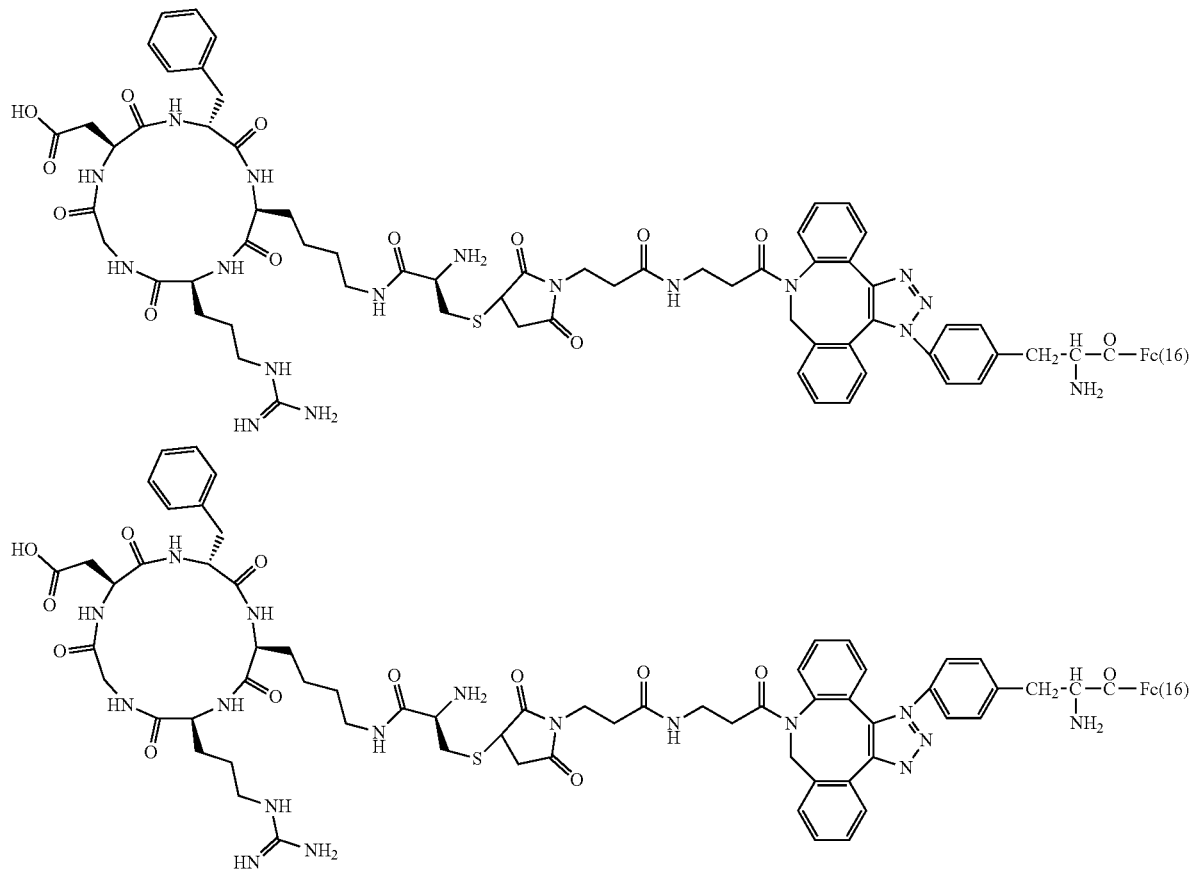

Figure 7:
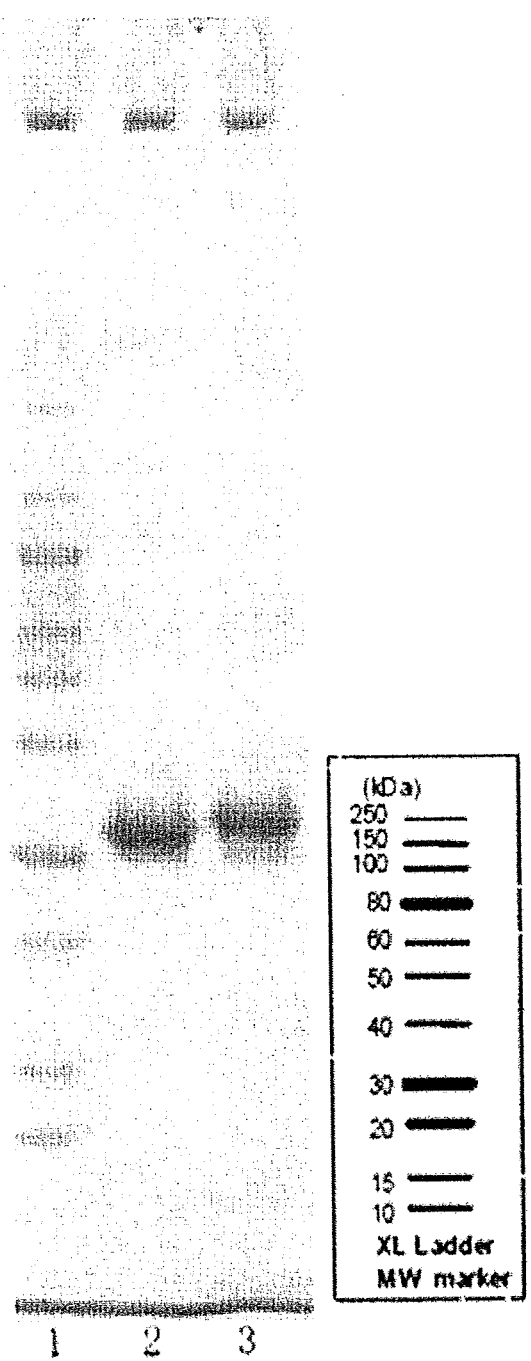
FIG. 7 is a drawing illustrating an SDS-PAGE evaluation of the rate of conversion into an Fc protein derivative in the synthesis of an Fc protein derivative added with an unnatural cyclic peptide as a substance of interest (Reaction B in FIG. 1). The synthesis of the Fc protein derivative added with the substance of interest was carried out by a reaction between the azide group-containing Fc protein and the substance of interest based on SPAAC reaction. Lane 1: molecular weight marker; lane 2: Fc protein Fc(16) before the reaction (negative control); lane 3: reaction mixture in the synthesis of the Fc protein derivative added with the substance of interest.

The result obtained by analyzing the obtained reaction mixture by SDS-PAGE (Mini-PROTEAN TGX gel, 4 to 20%, BIO-RAD; under reducing conditions; staining by Coomassie Brilliant Blue G-250 Stain) is illustrated in FIG. 7. From the result, it was recognized that the SPAAC reaction between the present peptide and an azide group-containing Fc protein progresses at extremely high reaction efficiency.

The reaction mixture was repeatedly subjected to, 5 times in total, concentration by ultrafiltration (Vivaspin 500, 10 k MWCO) and dilution with 20 mM ammonium acetate (pH 6.5) for buffer replacement. The resulting solution (14 µL) was added and mixed with 7 mM TCEP aqueous solution (4 µL) and acetonitrile (14 µL). After allowing it to stand for 30 minutes at room temperature, an ESI-TOFMS analysis was carried out. The results are shown below.

Molecular weight of Fc protein derivative added with a non-natural cyclic peptide (attached with G0 glycan):
  Theoretically calculated value: 29413.7
  ESI-TOFMS measured value: 29412.5

Example 9: Method of Producing Fc Protein Derivative Added with Non-Natural Linear Peptide Based on SPAAC Reaction (9-1) Preparation of Substance of Interest Added with Ring Having Triple Bond Between Carbon Atoms (Non-Natural Linear Peptide-DBCO Adduct)

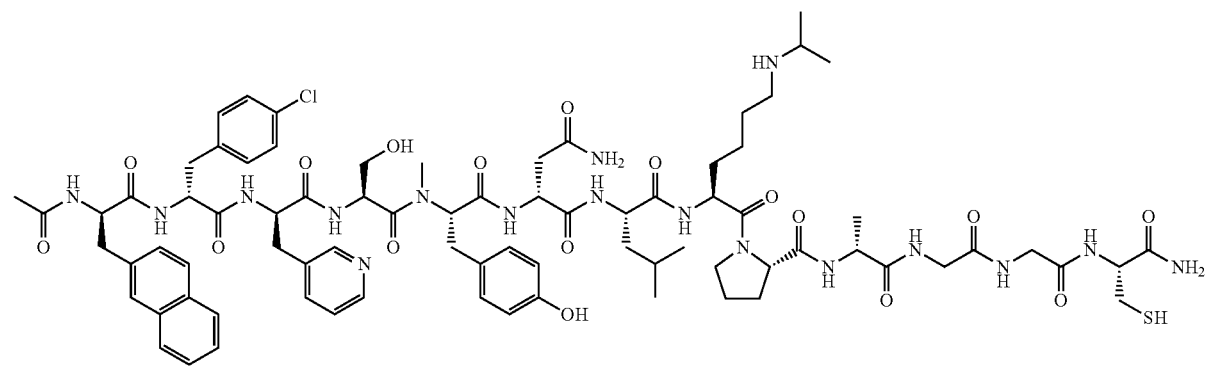 [SMILES: CC(=O)N[C@H](Cc1ccc2ccccc2c1)C(=O)N[C@H](Cc1ccc(Cl)cc1)C(=O)N[C@H](Cc1cccnc1)C(=O)N[C@@H](CO)C(=O)N(C)[C@@H](Cc1ccc(O)cc1)C(=O)N[C@H](CC(N)=O)C(=O)N[C@@H](CC(C)C)C(=O)N[C@@H](CCCCNC(C)C)C(=O)N1CCC[C@H]1C(=O)N[C@H](C)C(=O)NCC(=O)NCC(=O)N[C@@H](CS)C(N)=O]

As a substance of interest, 16.5 mg of a non-natural linear peptide of the above formula were dissolved in 826 µL of water, and to 576 µL of the resulting solution, 26.4 µL of DBCO (dibenzocyclooctyne)-maleimide (Tokyo Chemical Industries, 40 mM in DMSO) and 165.6 µL of DMSO were added and admixed with one another followed by shaking for 20 hours at room temperature. To the resultant, 8.8 µL of DBCO (dibenzocyclooctyne)-maleimide (Tokyo Chemical Industries, 40 mM in DMSO) and 100 µL of DMSO were additionally added and admixed with one another followed by shaking for 3.5 hours at room temperature. The reaction mixture was purified by fractional HPLC (Inertsil ODS-3, φ20×250 mm, eluent A; 100 mM ammonium acetate aqueous solution, eluent B; acetonitrile, linear gradient of from 45% B to 65% B). The obtained fraction was freeze-dried to obtain 4.5 mg of a non-natural linear peptide-DBCO adduct of the following formula. ESI-TOFMS (positive mode) m/z; 2060.9

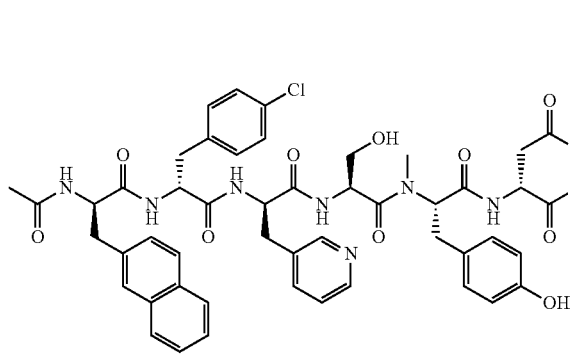
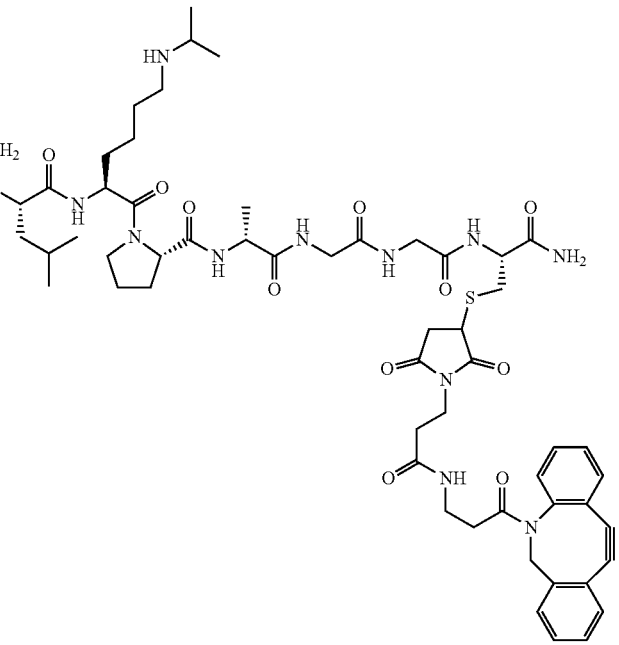

(9-2) Preparation of Fc Protein Derivative Added with Substance of Interest

To 6.6 μL of a solution of the azide group-containing Fc protein (containing 50 μg of azide group-containing Fc protein), 4.8 μL, of 0.1 M sodium phosphate buffer (pH 7.0), 20 μL of water, and 7.4 μL of a 2.5 mM solution of non-natural linear peptide-DBCO adduct obtained in (9-1) were added, and shaken for 19 hours at 25° C. After that, 20 μL of water and 6 μL of DMSO were additionally added and admixed with one another followed by shaking for 4 hours at 25° C. Thereby, an Fc protein derivative added with a non-natural linear peptide resulting from a reaction of an azide group-containing Fc protein and a non-natural linear peptide was obtained (following two types represented by the formula shown below are considered as an addition mode of azide group to DBCO).

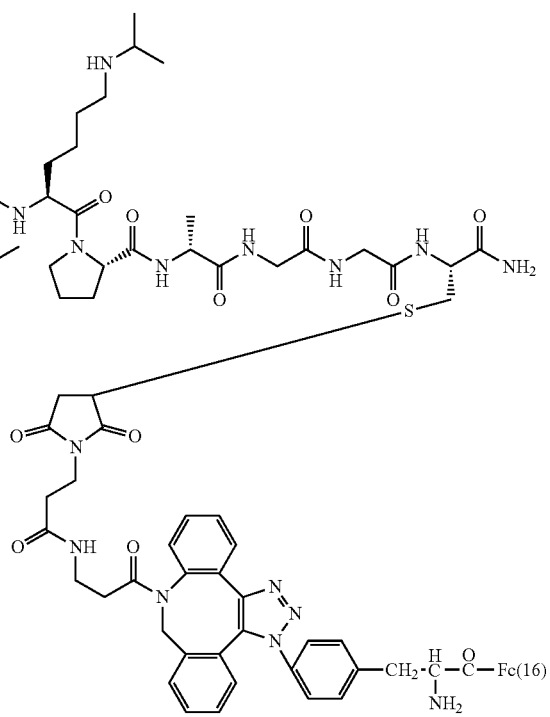

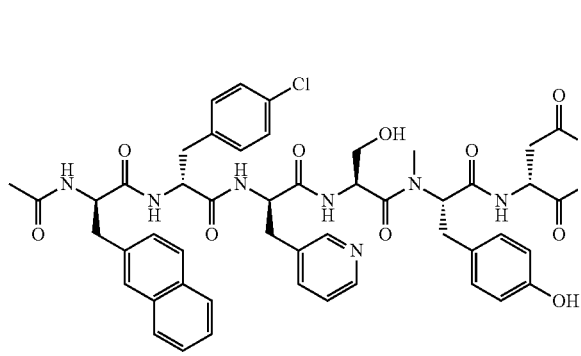
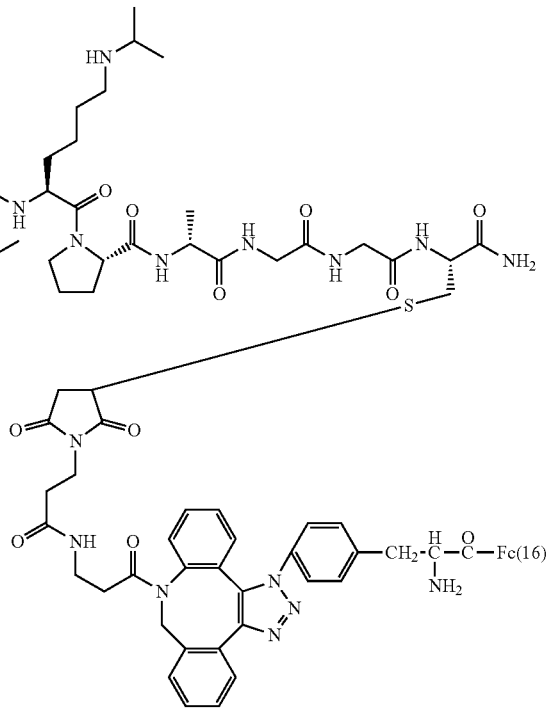

Figure 8:
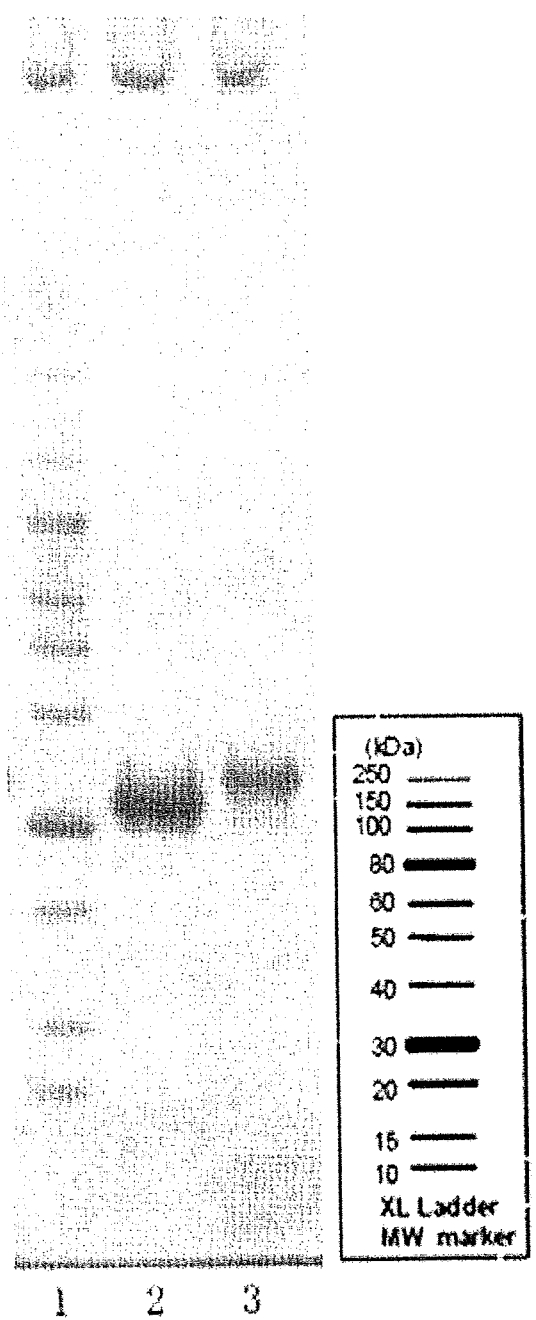
FIG. 8 is a drawing illustrating an SDS-PAGE evaluation of the rate of conversion into an Fc protein derivative in the synthesis of an Fc protein derivative added with an unnatural linear peptide as a substance of interest (Reaction B in FIG. 1). The synthesis of the Fc protein derivative added with the substance of interest was carried out by a reaction between the azide group-containing Fc protein and the substance of interest based on SPAAC reaction. Lane 1: molecular weight marker; lane 2: Fc protein Fc(16) before the reaction (negative control); lane 3: reaction mixture in the synthesis of the Fc protein derivative added with the substance of interest.

The result obtained by analyzing the obtained reaction mixture by SDS-PAGE (Mini-PROTEAN TGX gel, 4 to 20%, BIO-RAD; under reducing conditions; staining by Coomassie Brilliant Blue G-250 Stain) is illustrated in FIG. 8. From the result, it was recognized that the SPAAC reaction between the present peptide and an azide group-containing Fc protein progresses at extremely high reaction efficiency. The reaction mixture was repeatedly subjected to, 5 times in total, concentration by ultrafiltration (Vivaspin 500, 10 k MWCO) and dilution with 20 mM ammonium acetate (pH 6.5) for buffer replacement. The resulting solution (14 μL) was added and mixed with 7 mM TCEP aqueous solution (4 μL) and acetonitrile (14 μL). After allowing it to stand for 30 minutes at room temperature, an ESI-TOFMS analysis was carried out. The results are shown below.

Molecular weight of Fc protein derivative added with a non-natural linear peptide (attached with G0 glycan):

Theoretically calculated value: 30340.2
ESI-TOFMS measured value: 30339.5

Example 10: Method of Producing Fc Protein Derivative Added with Oligonucleic Acid Based on SPAAC Reaction (10-1) Preparation of Substance of Interest Added with Ring Having Triple Bond Between Carbon Atoms (Oligonucleic Acid-DBCO Adduct)

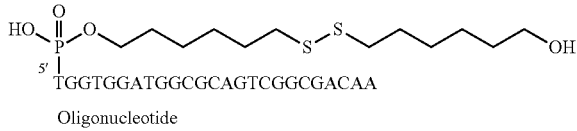

(SEQ ID NO: 21)

Oligonucleotide

As a substance of interest, 33.8 mg of an oligonucleic acid of the above formula (DNA, SEQ ID NO: 21) which was designed on the basis of the report by Orava (ACS Chem. Biol. 2013, 8, 170, which is incorporated herein by reference in its entirety) were dissolved in 6.77 mL of water, and to 5.77 mL of the resulting solution, 23.1 mL of 10 mM Tris-HCl, 1 mM EDTA, pH 8.0 and 28.8 mL of a 2:1 mixture solution of 0.12 M DTT aqueous solution and 0.5 M sodium phosphate buffer (pH 8.0) were added followed by shaking overnight at room temperature. The resultant was repeatedly subjected to, 4 times in total, concentration by ultrafiltration (Amicon Ultra-15, 3 k MWCO) and dilution with water for solvent replacement. The resultant was added with 88.8 μL of DBCO (dibenzocyclooctyne)-maleimide (Tokyo Chemical Industries, 40 mM in DMSO) and 600 μL of DMSO and admixed with one another followed by shaking overnight at room temperature. The reaction mixture was repeatedly subjected to, 4 times in total, concentration by ultrafiltration (Amicon Ultra-15, 3 k MWCO) and dilution with water for solvent replacement. The obtained solution was freeze-dried to obtain 21.1 mg of an oligonucleic acid-DBCO adduct of the following formula. ESI-TOFMS (negative mode) calculated; 8411.7, measured m/z; 1681.3, 2101.9.

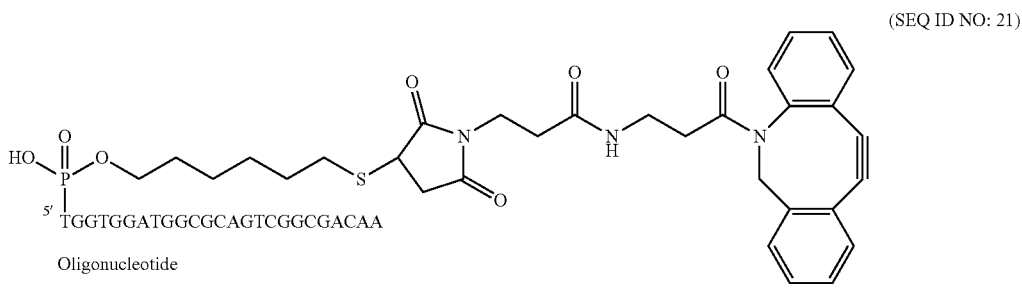

(SEQ ID NO: 21)

Oligonucleotide (10-2) Preparation of Fc Protein Derivative Added with Substance of Interest To 6.6 μL of a solution of the azide group-containing Fc protein (containing 50 μg of azide group-containing Fc protein), 24.4 μL of 0.1 M sodium phosphate buffer (pH 7.0) and 7.4 μL of a 2.5 mM solution of an adduct obtained in (10-1) were added, and shaken overnight at 25° C. Thereby, an Fc protein derivative added with a substance of interest resulting from a reaction of an azide group-containing Fc protein and an oligonucleic acid-DBCO adduct was obtained (the two types of addition modes of azide group to DBCO represented by the formula are considered).

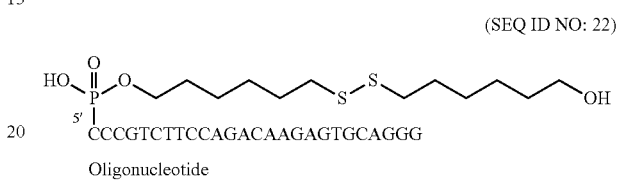

(SEQ ID NO: 22)

Oligonucleotide

As a substance of interest, 27.8 mg of an oligonucleic acid of the above formula (DNA, SEQ ID NO: 22) which was designed on the basis of the report by Potty (Biopolymers

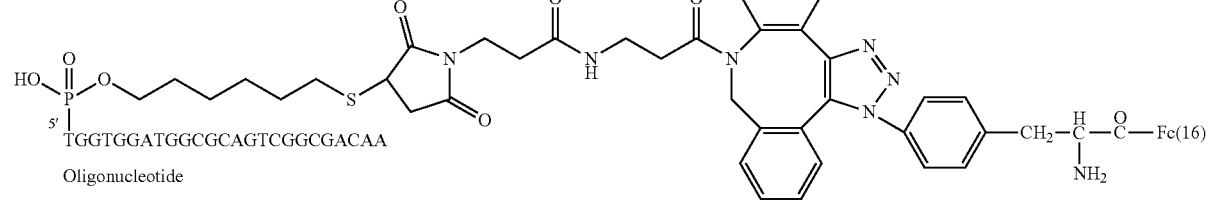

(SEQ ID NO: 21)

Oligonucleotide

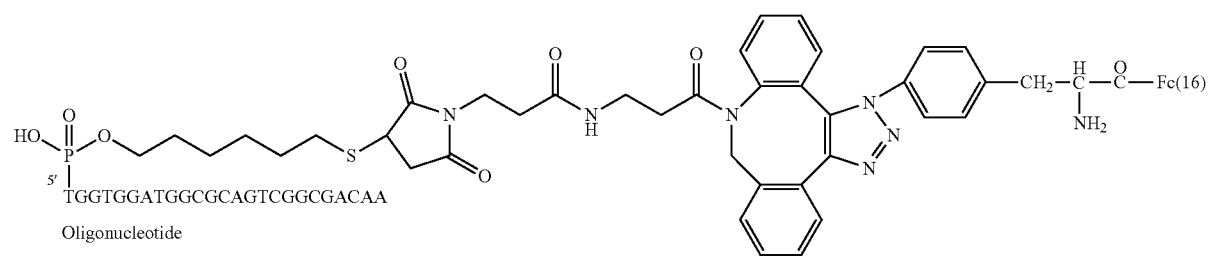

(SEQ ID NO: 21)

Oligonucleotide

Figure 9:
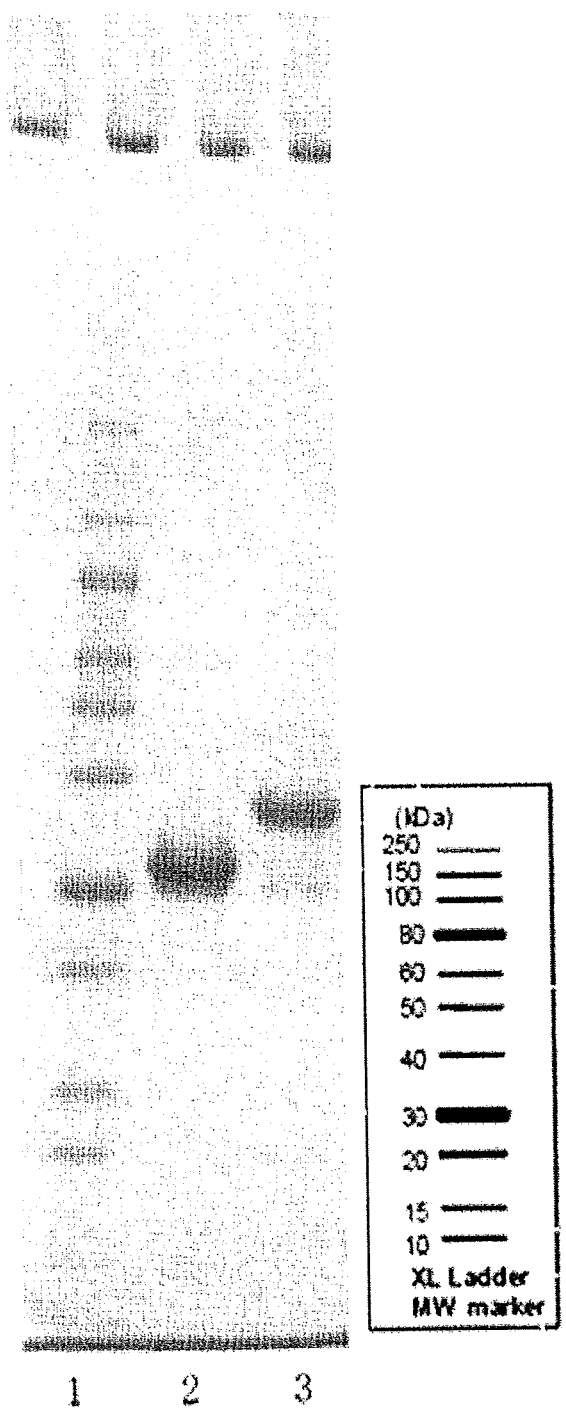
FIG. 9 is a drawing illustrating an SDS-PAGE evaluation of the rate of conversion into an Fc protein derivative in the synthesis of an Fc protein derivative added with an oligonucleic acid (SEQ ID NO: 21) as a substance of interest (Reaction B in FIG. 1). The synthesis of the Fc protein derivative added with the substance of interest was carried out by a reaction between the azide group-containing Fc protein and the substance of interest based on SPAAC reaction. Lane 1: molecular weight marker; lane 2: Fc protein Fc(16) before the reaction (negative control); lane 3: reaction mixture in synthesis of an Fc protein derivative added with a substance of interest.

The result obtained by analyzing the obtained reaction mixture by SDS-PAGE (Mini-PROTEAN TGX gel, 4 to 20%, BIO-RAD; under reducing conditions; staining by Coomassie Brilliant Blue G-250 Stain) is illustrated in FIG. 9. From the result, it was recognized that the SPAAC reaction between the present oligonucleic acid and an azide group-containing Fc protein progresses at extremely high reaction efficiency.

Example 11: Method of Producing Fc Protein Derivative Added with Oligonucleic Acid Based on SPAAC Reaction (11-1) Preparation of Substance of Interest Added with Ring Having Triple Bond Between Carbon Atoms (Oligonucleic Acid-DBCO Adduct)

2009, 91 (2), 145) were dissolved in 5.55 mL of water, and to 4.55 mL of the resulting solution, 18.2 mL of 10 mM Tris-HCl, 1 mM EDTA, pH 8.0 and 22.8 mL of a 2:1 mixture solution of 0.12 M DTT aqueous solution and 0.5 M sodium phosphate buffer (pH 8.0) were added followed by shaking overnight at room temperature. The resultant was repeatedly subjected to, 4 times in total, concentration by ultrafiltration (Amicon Ultra-15, 3 k MWCO) and dilution with water for solvent replacement. The resultant was added with 68.4 μL of DBCO (dibenzocyclooctyne)-maleimide (Tokyo Chemical Industries, 40 mM in DMSO) and 600 μL of DMSO and admixed with one another followed by shaking overnight at room temperature. The reaction mixture was repeatedly subjected to, 4 times in total, concentration by ultrafiltration (Amicon Ultra-15, 3 k MWCO) and dilution with water for solvent replacement. The obtained solution was freeze-dried to obtain 24.7 mg of an oligonucleic acid-DBCO adduct of the following formula. ESI-TOFMS (negative mode) calculated; 8604.8, measured m/z; 1719.9, 2150.1.

INDUSTRIAL APPLICABILITY

The Fc protein derivative of the present invention is useful as a pharmaceutical agent or a chemical reagent.

(SEQ ID NO: 22)

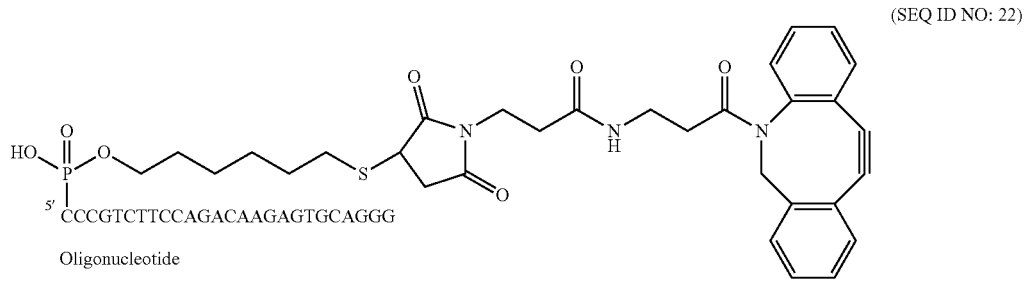

Oligonucleotide (11-2) Preparation of Fc Protein Derivative Added with Substance of Interest To 6.6 µL of a solution of the azide group-containing Fc protein (containing 50 µg of azide group-containing Fc protein), 24.4 µL of 0.1 M sodium phosphate buffer (pH 7.0) and 7.4 µL of a 2.5 mM solution of an adduct obtained in (11-1) were added, and shaken overnight at 25° C. Thereby, an Fc protein derivative added with a substance of interest resulting from a reaction of an azide group-containing Fc protein and an oligonucleic acid-DBCO adduct was obtained (following two types represented by the formula shown below are considered as an addition mode of azide group to DBCO).

The azide group-containing Fc protein of the present invention is useful as an intermediate for producing the Fc protein derivative of the present invention, for example.

The Fc protein of the present invention, which has a peptide linker consisting of 16 amino acid residues at/on the N-terminus, is useful as an intermediate for producing the Fc protein derivative of the present invention, for example.

Where a numerical limit or range is stated herein, the endpoints are included. Also, all values and subranges within a numerical limit or range are specifically included as if explicitly written out.

As used herein the words "a" and "an" and the like carry the meaning of "one or more."

(SEQ ID NO: 22)

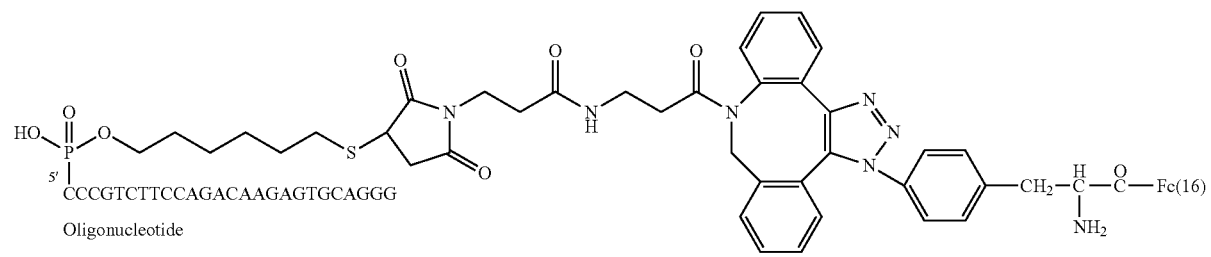

Oligonucleotide (SEQ ID NO: 22)

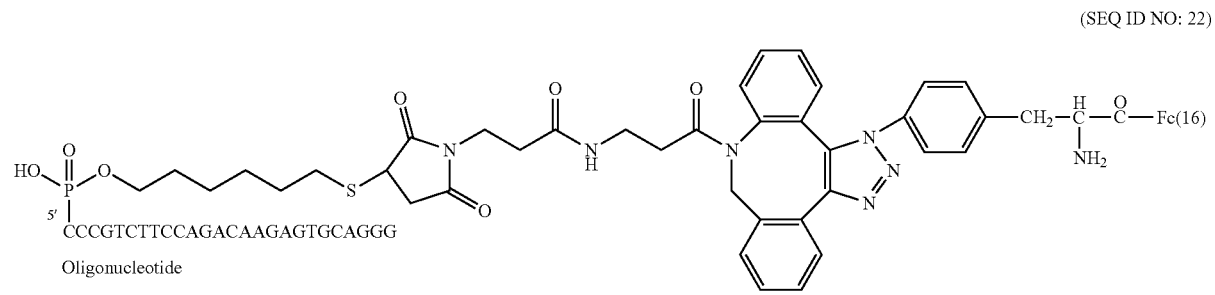

Oligonucleotide

Figure 10:
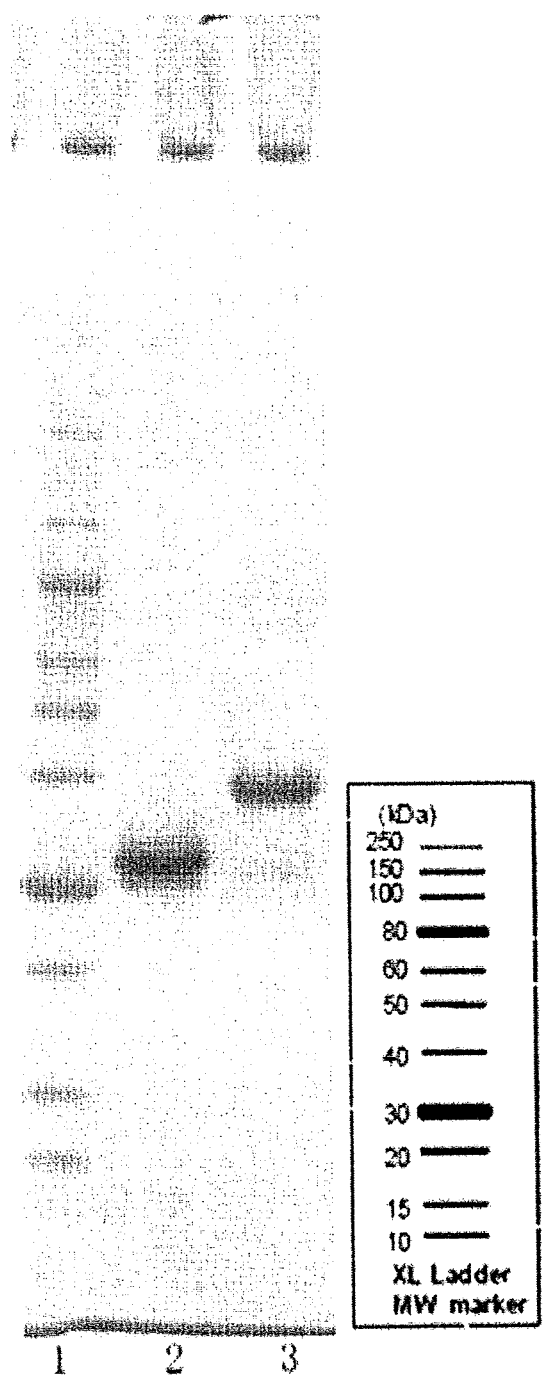
FIG. 10 is a drawing illustrating an SDS-PAGE evaluation of the rate of conversion into an Fc protein derivative in the synthesis of an Fc protein derivative added with an oligonucleic acid (SEQ ID NO: 22) as a substance of interest (Reaction B in FIG. 1). The synthesis of the Fc protein derivative added with the substance of interest was carried out by a reaction between the azide group-containing Fc protein and the substance of interest based on SPAAC reaction. Lane 1: molecular weight marker; lane 2: Fc protein Fc(16) before the reaction (negative control); lane 3: reaction mixture in the synthesis of the Fc protein derivative added with the substance of interest.

The result obtained by analyzing the obtained reaction mixture by SDS-PAGE (Mini-PROTEAN TGX gel, 4 to 20%, BIO-RAD; under reducing conditions; staining by Coomassie Brilliant Blue G-250 Stain) is illustrated in FIG. 10. From the result, it was recognized that the SPAAC reaction between the present oligonucleic acid and an azide group-containing Fc protein progresses at extremely high reaction efficiency.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. An azide group-containing Fc protein represented by formula (1):

$$N_3\text{-}L_a\text{-}Phe\text{-}L_b\text{-}Fc \tag{1}$$

wherein $N_3$ represents an azide group;

$L_a$ represents a bond or a divalent group;

Phe represents a residue of phenylalanine or a derivative thereof;

$L_b$, represents a lysine residue or an arginine residue, or a peptide linker containing two or more amino acid residues having a lysine residue or arginine residue at the N-terminus; and Fc represents an Fc protein.

2. The azide group-containing Fc protein according to claim 1, wherein the peptide linker contains 4 to 30 amino acid residues.

3. The azide group-containing Fc protein according to claim 2, wherein the peptide linker contains 16 amino acid residues.

4. The azide group-containing Fc protein according to claim 1, wherein the azide group-containing Fc protein is represented by formula (1-1):

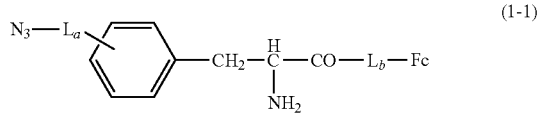

(1-1)

wherein the benzene ring my be further substituted.

5. The azide group-containing Fc protein according to claim 1, wherein the Fc protein is derived from an Fc region of a mammalian antibody.

6. The azide group-containing Fc protein according to claim 5, wherein the mammalian antibody is a human antibody.

7. The azide group-containing Fc protein according to claim 1, wherein the Fc protein is derived from an Fc region of an IgG antibody.

8. The azide group-containing Fc protein according to claim 1, wherein the Fc protein is selected from the group consisting of:

(a) a protein comprising the amino acid sequence of SEQ ID NO: 1;

(b) a protein comprising an amino acid sequence comprising one or several amino acid residue mutations selected from the group consisting of amino acid residue deletions, substitutions, additions, and insertions in the amino acid sequence of SEQ ID NO: 1; and (c) a protein comprising an amino acid sequence having least 90% or more homology to the amino acid sequence of SEQ ID NO:1.

9. A method of producing azide group-containing Fc protein, comprising reacting an azide group-containing phenylalanine derivative represented by formula (2):

$$N_3\text{-}L_a\text{-}Phe \tag{2}$$

wherein $N_3$ represents an azide group;

$L_a$ represents a bond or a divalent group; and

Phe represents phenylalanine or a derivative thereof;

with an Fc protein having a lysine residue or an arginine residue at the N-terminus represented by formula (3):

$$L_b\text{-}Fc \tag{3}$$

wherein represents a lysine residue or an arginine residue, or a peptide linker consisting of two or more amino acid residues having a lysine residue or an arginine residue at the N-terminus; and Fc represents an Fc protein;

in the presence of phenylalanyl tRNA, aminoacyl tRNA synthetase, and leucyl/phenylalanyl tRNA transferase, to obtain an azide group-containing Fc protein represented by formula (1):

$$N_3\text{-}L_a\text{-}Phe\text{-}L_b\text{-}Fc \tag{1}$$

wherein $N_3$ and $L_a$ are the same as in formula (2);

Phe represents a residue of phenylalanine or a derivative thereof; and $L_b$ and Fc are the same as in formula (3).

10. An Fc protein derivative fused with a substance of interest represented by formula (4):

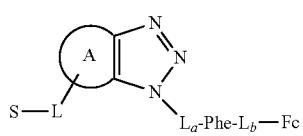

(4)

wherein S represents a substance of interest;

L represents a bond or a divalent group;

ring A represents a ring fused to triazole:

$L_a$ represents a bond or a divalent group;

Phe represents a residue of phenylalanine or a derivative thereof;

$L_b$ represents a lysine residue or an arginine residue, or a peptide linker consisting of two or more amino acid residues having a lysine residue or an arginine residue at the N-terminus; and Fc represents an Fc protein.

11. The Fr protein derivative according to claim 10, wherein the ring A is a 7- or 8-membered ring or a fused ring of a 7- or 8-membered ring and other ring.

12. The Fc protein derivative according to claim 10, wherein the substance of interest is a polymeric substance.

13. The Fc protein derivative according to claim 10, wherein the substance of interest is a peptide, a saccharide, or a nucleotide.

14. The Fc protein derivative according to claim 10, wherein the substance of interest is a peptide having a cysteine residue at the C-terminus.

15. A method of producing an Fc protein derivative fused with a substance of interest, comprising
reacting a substance of interest derivatized with a ring having a triple bond between carbon atoms represented by formula (5):

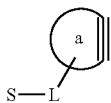
(5)

where S represents a substance of interest;
L represents a bond or a divalent group; and
ring a represents a ring having a triple bond between carbon atoms;
with an azide group-containing Fc protein represented b formula (1):

N$_3$-L$_a$-Phe-L$_b$-Fc (1)

wherein N$_3$ represents an azide group;
L$_a$ represents a bond or a divalent group;
Phe represents a residue of phenylalanine or a derivative thereof;
L$_b$ represents a lysine residue or an arginine residue, or a peptide linker consisting of two or more amino acid residues having a lysine residue or an arginine residue at the N-terminus; and
Fc represents an Fc protein;
to obtain an Fc protein derivative fused with a substance of interest represented by formula (4):

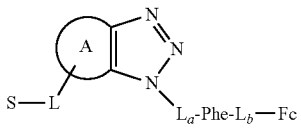
(4)

wherein S and L are the same as in the formula (5);
ring A represents a ring fused to triazole; and
L$_a$, Phe, L$_b$, and Fc are the same as in formula (1).

16. The method according to claim 15, wherein the ring having a triple bond between carbon atoms is a 7- or 8-membered ring or a fused ring of a 7- or 8-membered ring and other ring.

17. The method according to claim 15, further comprising reacting the substance of interest with a reagent comprising a ring having a triple bond between carbon atoms to yield a substance of interest derivatized with a ring having a triple bond between carbon atoms.

18. A method of producing an Fc protein derivative fused with a substance of interest, comprising:
(A) reacting an azide group-containing phenylalanine derivative represented by formula (2):

N$_3$-L$_a$-Phe (2)

wherein N$_3$ represents an azide group:
L$_a$ represents a bond or a divalent group; and
Phe represents phenylalanine or a derivative thereof;
with an Fc protein having a lysine residue or an arginine residue at the N-terminus represented by formula (3):

L$_b$-Fc (3)

wherein L$_b$ represents a lysine residue or an arginine residue, or a peptide linker consisting of two or more amino acid residues having a lysine residue or an arginine residue at the N-terminus; and
Fc represents an Fc protein;
in the presence of phenylalanyl tRNA, aminoacyl tRNA synthetase, and leucyl/phenalalanyl tRNA transferase, to obtain an azide group-containing Fc protein represented by formula (1):

N$_3$-L$_a$-Phe-L$_b$-Fc (1)

wherein N$_3$ and L$_a$ are the same as in formula (2);
Phe represents a residue of phenylalanine or a derivative thereof; and
L$_b$ and Fc are the same as in formula (3); and
(B) reacting a substance of interest derivatized with a ring having a triple bond between carbon atoms represented by formula (5):

(5)

wherein S represents a substance of interest:
L represents a bond or a divalent group; and
ring a represents a ring baying a triple bond between carbon atoms;
with the azide group-containing Fc protein represented by formula (1),
to obtain an Fc protein derivative fused with a substance of interest represented by formula (4):

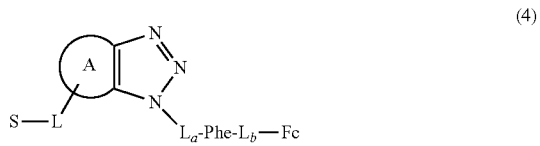
(4)

wherein S and L are the same as in formula (5);
ring a represents a ring fused to triazole; and
L$_a$, Phe, L$_b$, and Fc are the same as in formula (1).

19. An azide group-containing Fc protein having an azide group-containing phenylalanine derivative at the N-terminus of the azide group-containing Fc protein via a peptide linker containing 16 amino acid residues, wherein the N terminal amino acid residue of the peptide linker is a lysine residue or an arginine residue.

20. A method of producing azide group-containing Fc protein having an azide group-containing phenylalanine derivative at the N-terminus of the azide group-containing Fc protein via a peptide linker containing 16 amino acid residues, wherein the N terminal amino acid residue of the peptide linker is a lysine residue or an arginine residue,
said method comprising reacting an azide group-containing phenylalanine derivative with the Fc protein having the peptide linker at the N-terminus, in the presence of phenylalanyl tRNA, aminoacyl tRNA Synthetase, and leucyl/phenylalanyl tRNA transferase, to obtain the azide group-containing Fc protein.

* * * * *

SEQUENCE LISTING

<160> NUMBER OF SEQ ID NOS: 22

<210> SEQ ID NO 1
<211> LENGTH: 222
<212> TYPE: PRT
<213> ORGANISM: Artificial Sequence
<220> FEATURE:
<223> OTHER INFORMATION: Cys-Fc protein

<400> SEQUENCE: 1

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 2
<211> LENGTH: 242
<212> TYPE: PRT
<213> ORGANISM: Artificial Sequence
<220> FEATURE:
<223> OTHER INFORMATION: Leader sequence-added Fc protein

<400> SEQUENCE: 2

Met Glu Thr Asp Thr Leu Leu Leu Trp Val Leu Leu Leu Trp Val Pro
1               5                   10                  15

Gly Ser Thr Gly Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

```
Asn Ala Lys Thr Lys Pro Arg Glu Glu Gln Tyr Asn Ser Thr Tyr Arg
            85                  90                  95
Val Val Ser Val Leu Thr Val Leu His Gln Asp Trp Leu Asn Gly Lys
        100                 105                 110
Glu Tyr Lys Cys Lys Val Ser Asn Lys Ala Leu Pro Ala Pro Ile Glu
            115                 120                 125
Lys Thr Ile Ser Lys Ala Lys Gly Gln Pro Arg Glu Pro Gln Val Tyr
130                 135                 140
Thr Leu Pro Pro Ser Arg Asp Glu Leu Thr Lys Asn Gln Val Ser Leu
145                 150                 155                 160
Thr Cys Leu Val Lys Gly Phe Tyr Pro Ser Asp Ile Ala Val Glu Trp
                165                 170                 175
Glu Ser Asn Gly Gln Pro Glu Asn Asn Tyr Lys Thr Thr Pro Pro Val
            180                 185                 190
Leu Asp Ser Asp Gly Ser Phe Phe Leu Tyr Ser Lys Leu Thr Val Asp
        195                 200                 205
Lys Ser Arg Trp Gln Gln Gly Asn Val Phe Ser Cys Ser Val Met His
    210                 215                 220
Glu Ala Leu His Asn His Tyr Thr Gln Lys Ser Leu Ser Leu Ser Pro
225                 230                 235                 240
Gly Lys

<210> SEQ ID NO 3
<211> LENGTH: 20
<212> TYPE: PRT
<213> ORGANISM: Artificial Sequence
<220> FEATURE:
<223> OTHER INFORMATION: Leader sequence

<400> SEQUENCE: 3

Met Glu Thr Asp Thr Leu Leu Leu Trp Val Leu Leu Leu Trp Val Pro
1               5                   10                  15
Gly Ser Thr Gly
            20

<210> SEQ ID NO 4
<211> LENGTH: 4
<212> TYPE: PRT
<213> ORGANISM: Artificial Sequence
<220> FEATURE:
<223> OTHER INFORMATION: Peptide linker

<400> SEQUENCE: 4

Lys Thr His Thr
1

<210> SEQ ID NO 5
<211> LENGTH: 8
<212> TYPE: PRT
<213> ORGANISM: Artificial Sequence
<220> FEATURE:
<223> OTHER INFORMATION: Peptide linker

<400> SEQUENCE: 5

Lys Ser Ser Asp Lys Thr His Thr
1               5

<210> SEQ ID NO 6
<211> LENGTH: 12
<212> TYPE: PRT
<213> ORGANISM: Artificial Sequence
```

<220> FEATURE:
<223> OTHER INFORMATION: Peptide linker

<400> SEQUENCE: 6

Lys Val Glu Pro Lys Ser Ser Asp Lys Thr His Thr
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Peptide linker

<400> SEQUENCE: 7

Lys Lys Val Glu Pro Lys Ser Ser Asp Lys Thr His Thr
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Peptide linker

<400> SEQUENCE: 8

Lys Val Asp Lys Lys Val Glu Pro Lys Ser Ser Asp Lys Thr His Thr
1               5                   10                  15

<210> SEQ ID NO 9
<211> LENGTH: 40
<212> TYPE: PRT
<213> ORGANISM: Artificial Sequence
<220> FEATURE:
<223> OTHER INFORMATION: Artificial peptide "Exenatide-Cys" to be fused
      with Fc protein. Cys residue at C-terminus has CONH2 rather than
      COOH

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Cys
        35                  40

<210> SEQ ID NO 10
<211> LENGTH: 6
<212> TYPE: PRT
<213> ORGANISM: Artificial Sequence
<220> FEATURE:
<223> OTHER INFORMATION: Amino acid sequence recognized by ProTEV
      protease

<400> SEQUENCE: 10

Glu Asn Leu Tyr Phe Gln
1               5

<210> SEQ ID NO 11
<211> LENGTH: 27
<212> TYPE: DNA
<213> ORGANISM: Artificial Sequence
<220> FEATURE:
<223> OTHER INFORMATION: Primer

<400> SEQUENCE: 11
cgagccacca ggcaggcggg aaaatcg                                      27

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12 cgatttccc gcctgcctgg tggctcg                                       27

<210> SEQ ID NO 13
<211> LENGTH: 23
<212> TYPE: DNA
<213> ORGANISM: Artificial Sequence
<220> FEATURE:
<223> OTHER INFORMATION: Primer

<400> SEQUENCE: 13
cccgcttgat cattcctta agg                                           23

<210> SEQ ID NO 14
<211> LENGTH: 36
<212> TYPE: DNA
<213> ORGANISM: Artificial Sequence
<220> FEATURE:
<223> OTHER INFORMATION: Primer

<400> SEQUENCE: 14
aatgggccct tggtacccc taataatat cggtcc                              36

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
cgtgctctag gggaaccgtg cgttccc                                      27

<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
gggaacgcac ggttcccta gagcacg                                       27

<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
cgacgctgaa gttgtagaga tcatccg                                      27

<210> SEQ ID NO 18
<211> LENGTH: 27
<212> TYPE: DNA
<213> ORGANISM: Artificial Sequence

```
<220> FEATURE:
<223> OTHER INFORMATION: Primer

<400> SEQUENCE: 18
cggatgatct ctacaacttc agcgtcg                                              27

<210> SEQ ID NO 19
<211> LENGTH: 681
<212> TYPE: DNA
<213> ORGANISM: Artificial Sequence
<220> FEATURE:
<223> OTHER INFORMATION: Lys-Fc protein
<220> FEATURE:
<221> NAME/KEY: CDS
<222> LOCATION: (1)..(681)

<400> SEQUENCE: 19 aag acc cac acc tgc cct cca tgt cct gct cca gag ttg ctc ggt ggt      48
Lys Thr His Thr Cys Pro Pro Cys Pro Ala Pro Glu Leu Leu Gly Gly
1               5                   10                  15 ccg tcc gtg ttc ttg ttc cct cct aag cct aag gat acc ctg atg atc      96
Pro Ser Val Phe Leu Phe Pro Pro Lys Pro Lys Asp Thr Leu Met Ile
            20                  25                  30 tct cgc acc cca gaa gtt acc tgc gtg gtc gtt gat gtg tcc cac gaa     144
Ser Arg Thr Pro Glu Val Thr Cys Val Val Asp Val Ser His Glu
        35                  40                  45 gat cca gag gtg aag ttc aac tgg tac gtc gat ggt gtt gaa gtg cac     192
Asp Pro Glu Val Lys Phe Asn Trp Tyr Val Asp Gly Val Glu Val His
    50                  55                  60 aac gca aag acc aag cca cgt gaa gag cag tac aac tct acc tac cgc     240
Asn Ala Lys Thr Lys Pro Arg Glu Glu Gln Tyr Asn Ser Thr Tyr Arg
65                  70                  75                  80 gtc gtg tcc gtt ctt acc gtg ctg cac cag gat tgg ctg aac ggc aag     288
Val Val Ser Val Leu Thr Val Leu His Gln Asp Trp Leu Asn Gly Lys
                85                  90                  95 gaa tac aaa tgc aag gtg tcc aac aag gca ctg cca gct cca atc gaa     336
Glu Tyr Lys Cys Lys Val Ser Asn Lys Ala Leu Pro Ala Pro Ile Glu
            100                 105                 110 aag acc atc tcc aag gca aag ggt cag cca cgt gaa cca cag gtt tac     384
Lys Thr Ile Ser Lys Ala Lys Gly Gln Pro Arg Glu Pro Gln Val Tyr
        115                 120                 125 acc ctg cca ccg tct cgc gac gaa ctg acc aag aac cag gtg tcc ctg     432
Thr Leu Pro Pro Ser Arg Asp Glu Leu Thr Lys Asn Gln Val Ser Leu
    130                 135                 140 acc tgc ctg gtg aag ggt ttc tac cca tcc gac atc gca gtg gag tgg     480
Thr Cys Leu Val Lys Gly Phe Tyr Pro Ser Asp Ile Ala Val Glu Trp
145                 150                 155                 160 gaa tct aac ggc cag cca gag aac aac tac aag acc acc cca cct gtg     528
Glu Ser Asn Gly Gln Pro Glu Asn Asn Tyr Lys Thr Thr Pro Pro Val
                165                 170                 175 ctg gat tcc gac ggt tct ttc ttc ctg tac tcc aag ctg acc gtt gac     576
Leu Asp Ser Asp Gly Ser Phe Phe Leu Tyr Ser Lys Leu Thr Val Asp
            180                 185                 190 aag tct cgc tgg cag cag ggc aac gtt ttc tcc tgc tct gtg atg cac     624
Lys Ser Arg Trp Gln Gln Gly Asn Val Phe Ser Cys Ser Val Met His
        195                 200                 205 gag gca ctc cac aac cac tac acc cag aag tct ctc tct ctc tct cca     672
Glu Ala Leu His Asn His Tyr Thr Gln Lys Ser Leu Ser Leu Ser Pro
    210                 215                 220 ggc aaa taa                                                         681
Gly Lys
225
```

<210> SEQ ID NO 20
<211> LENGTH: 226
<212> TYPE: PRT
<213> ORGANISM: Artificial Sequence
<220> FEATURE:
<223> OTHER INFORMATION: Synthetic Construct

<400> SEQUENCE: 20

```
Lys Thr His Thr Cys Pro Pro Cys Pro Ala Pro Glu Leu Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Asp Glu Leu Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225
```

<210> SEQ ID NO 21
<211> LENGTH: 25
<212> TYPE: DNA
<213> ORGANISM: Artificial Sequence
<220> FEATURE:
<223> OTHER INFORMATION: aptamer

<400> SEQUENCE: 21
tggtggatgg cgcagtcggc gacaa                                         25

<210> SEQ ID NO 22
<211> LENGTH: 26
<212> TYPE: DNA
<213> ORGANISM: Artificial Sequence

```
<220> FEATURE:
<223> OTHER INFORMATION: aptamer

<400> SEQUENCE: 22
cccgtcttcc agacaagagt gcaggg                                        26
```